(12) United States Patent
Skouv

(10) Patent No.: US 6,303,315 B1
(45) Date of Patent: Oct. 16, 2001

(54) ONE STEP SAMPLE PREPARATION AND DETECTION OF NUCLEIC ACIDS IN COMPLEX BIOLOGICAL SAMPLES

(75) Inventor: Jan Skouv, Espergærde (DK)

(73) Assignee: Exiqon A/S, Vedbaek (DK)

( * ) Notice: Subject to any disclaimer, the term of this patent is extended or adjusted under 35 U.S.C. 154(b) by 0 days.

(21) Appl. No.: 09/528,271

(22) Filed: Mar. 18, 2000

Related U.S. Application Data

(60) Provisional application No. 60/127,356, filed on Apr. 1, 1999.

(30) Foreign Application Priority Data

Mar. 18, 1999 (DK) ............................................ 1999 00384

(51) Int. Cl.$^7$ ...................................................... C12Q 1/68
(52) U.S. Cl. ..................... 435/6; 435/5; 435/6; 435/91.1; 435/91.2; 536/23.1; 536/24.3; 536/32; 536/33; 422/68.1
(58) Field of Search ................................. 435/6, 5, 91.2; 536/23.1, 24.3, 32, 33; 422/68.1

(56) References Cited

U.S. PATENT DOCUMENTS

| | | | |
|---|---|---|---|
| 5,821,060 | 10/1998 | Arlinghaus et al. ...................... | 435/6 |
| 5,942,391 | * 6/2000 | Zhang et al. .............................. | 435/6 |
| 6,077,673 | * 6/2000 | Zhang et al. .............................. | 435/6 |

FOREIGN PATENT DOCUMENTS

| | | |
|---|---|---|
| 0538194 B1 | 4/1999 | (EP) . |
| WO 92/20703 | 11/1992 | (WO) . |
| WO98/22489 | 5/1998 | (WO) . |
| WO98/39352 | 9/1998 | (WO) . |
| WO99/14226 | 3/1999 | (WO) . |

OTHER PUBLICATIONS

Tarkoy et al., *Helv. Chim. Acta*, 76:481 (1993).
Tarkoy et al., *Angew. Chem. Int. Ed. Engl.*, 32:1432 (1993).
Egli et al., *J. Am. Chem. Soc.*, 115:5855 (1993).
Tarkoy et al., *Helv. Chim. Acta*, 77:716 (1994).
Bolli et al., *Angew. Chem. Int. Ed. Engl.*, 34:694 (1995).
Bolli et al., *Helv. Chim. Acta*, 78:2077 (1995).
Litten et al., *Bioorg. Med. Chem. Lett.*, 5:1231 (1995).
Litten et al., *Helv. Chim. Acta*, 79:1129 (1996).
Bolli et al., *Chem. Biol.*, 3:197 (1996).
Bolli et al., *Nucleic Acids. Res.*, 24:4660 (1996).
K.H. Altmann et al., *Tetrahedron Lett.*, 35:2331 (1994).
K. H. Altmann et al., *Tetrahedron Lett.*, 35:7625 (1994).
Marquez et al., *J. Med. Chem.*, 39:3739 (1996).
Ezzitouni et al., *J. Chem. Soc., Perkin Trans.*, 1:1073 (1997).
Jones et al., *J. Am. Chem. Soc.*, 115:9816 (1993).
Wang et al., *Bioorg. Med. Chem. Lett.*, 7:229 (1997).
Yannopoulus et al., *Synlett*, 378 (1997).
CHIMA, 36th Congress, organized by the Swiss Chemical Society, Poster No. SB–B4: Steffens, R. and Leumann Ch. Tricyclo–DNA: synthesis, enzymatic stability, and pairing properties.
Nielsen, Master Thesis (Odense University, Denmark), p. 67–71 (1995).
Youssefyeh et al., *J. Org. Chem.*, 44:1301 (1979).
Jones et al., *J. Org. Chem.*, 44:1309 (1979).
Yang et al., *Tetrahedron Lett.*, 33:37 (1992).
Thrane et al., *Tetrahedron*, 51:10389 (1995).
Nielsen et al., *Bioorg. Med. Chem.*, 3:1493 (1995).
Freier et al., *Nucleic Acid Research*, 25:4429–4443 (1997).
Haly et al., *Synlett*, 687–689 (1996).
Zou et al., *Tetrahedron Lett.*, 37:941–944 (1996).
Herdewijn., *Liebigs Ann.*, 1337–1348 (1996).
Obika et al., *Tetrahedron Lett.*, 39:5401–5404 (1998).
Obika et al., *Tetrahedron Lett.*, 38:8735–8738 (1997).
7th Antisense Symposium, Nov. 21–22, 1997. Poster No. 32 and 33: Obika, D.N.; Morio, K. and Imanishi, T. Synthesis and properties of oligonucleotides containing novel bicyclic nucleosides with a fixed N–form sugar puckering.
CHIMA, 36th IUPAC Congress, organized by the Swiss Chemical Society. Poster No. SB–B12: Egtger, A. and Leumann Ch. Designe, synthesis and properties of bicyclo [3.2.1]–amino nucleic acids.
CHIMA, 36th IUPAC Congress, organized by the Swiss Chemical Society. Poster No. SB–B5: Epple, C. Ch., Pompizi, I. and Leumann Ch. Bicyclo [3.2.1]–DNA: an oligonucleotide analogue with a conformationally preorganized Phosphodiester backbone and a flexible sugar–base linkage.
Sep. 6–10, 1998: 13th International Round Table—Nucleoside, Nucleotides and their Biological Applications, Montpeilleir: Oral Communication 1: Wang, G. and Gunic, E. "Conformationally Locked Nucleoside Analogs. Synthesis of 2'–Deoxy–2'–C, 4'–C–Bridged Bicyclic Nucleoside".

(List continued on next page.)

Primary Examiner—W. Gary Jones
Assistant Examiner—Janell E. Taylor
(74) *Attorney, Agent, or Firm*—Peter F. Corless; Edwards & Angell, LLP

(57) ABSTRACT

A method for simultaneous release and detection of nucleic acids from complex biological samples is described. The invention relates to the combined use of lysis buffers containing strong chaotropic agents such as guanidine thiocyanate to facilitate cell lysis and release of cellular nucleic acids and to the use of a novel type of bicyclic nucleotide analogues, locked nucleic acid (LNA) to detect specific nucleic acids released during lysis by nucleic acid hybridisation. In particular methods are described for the covalent attachment of the catching LNA-oligo. Novel methods for sample preparation of e.g. polyadenylated mRNA species are also presented. The invention further addresses reagents for performing the methods as well as reagents and applications of the method.

65 Claims, 11 Drawing Sheets

OTHER PUBLICATIONS

Sep. 6–10, 1998: 13th International Round Table—Nucleoside, Nucleotides and their Biological Applications, Montpeilleir: Poster No. 288: Meldgaard, M. et al., "LNA (Locked Nucleic Acids): Synthesis and Thermal Denaturation Studies".

Sep. 6–10, 1998: 13th International Round Table—Nucleoside, Nucleotides and their Biological Applications, Montpeilleir: Oral Communication 1: Wang, G. and Gunic, E. "Conformationally Locked Nucleoside Analogs. Synthesis of 2'–Deoxy–2'–C, 4'–C–Bridged Bicyclic Nucleoside".

Sep. 6–10, 1998: 13th International Round Table—Nucleoside, Nucleotides and their Biological Applications, Montpeilleir: Poster No. 67: Nielsen, P. and Wengel, J. "A New Convergent Synthetic Approach Towards α–and β–LNA (Locked Nucleic Acids)".

Oct. 8, 1998: Antisense 98, Targeting the Molecularl Basis of Disease: Poster No. 24: Havsteen, M. et al., "LNA (Locked Nucleic Acids): A new Class of High Affinity Nucleic Acids With Prime Potential as Antisense and Antigene Agents".

Jan. 21, 1998: National Seminar on Perspectives in Interfacial Areas of Chemistry and Biology, Delhi University: Wengel, J. "LNA (Locked Nucleic Acids): Synthesis and High Affinity Nucleic Acid Recognition—Stop the Twisting."

Mar. 27, 1998: Workshop of Young European Bioorganic Chemists, Munchen: Wengel, J. "LNA (Locked Nucleic Acids): Synthesis and High Affinity Nucleic Acid Recognition—Stop the Twisting."

Aug. 20, 1988: Årsmødet for Center for Medicinsk Biotechnologi, KVL: Wengel, J. "LNA (Locked Nucleic Acids)"ations, Montpeilleir: Oral Communication 1: Wang, G. and Gunic, E. "Conformationally Locked Nucleoside Analogs. Synthesis of 2'–Deoxy–2'–C, 4'–C–Bridged Bycyclic Nucleoside".

Sep. 7, 1998: 13th International Round Table—Nucleoside, Nucleotides and their Biological Applications, Montpeilleir: Oral Communication 2: Wengel, J. "LNA (Locked Nucleic Acids)".

Sep. 8, 1998: Meeting in Lund, Sweden: Jakobsen, M. H. "LNA (Locked Nucleic Acids): A new Class of High Affinity Nucleic Acids With Prime Potential as Antisense and Antigene Agents".

Nielsen et al., *J. Chem. Soc., Perkin Trans.,* 1:3423–3433 (1997).

Nielsen et al., *Chem. Commun.,* 9:825–826 (1997).

Singh et al., *Chem. Commun.,* 9:455–456 (1998).
Koshkin et al., *Tetrahedron,* 54:360733630 (1998).
Koshkin et al., *Tetrahedron Lett.,* 39:4381–8384 (1998).
Singh et al., *Chem. Commun.,* 1237–1248 (1998).
Singh et al., *J. Org. Chem.,* 63:6078–6079 (1998).
Christensen et al., *J. Am. Chem. Soc.,* 120:5458–5463 (1998).
Koshkin et al., *J. Org. Chem.,* 63:2778–2781 (1998).
Kumar et al., *Bioorg. Med. Chem. Lett.,* 8:2219–2222 (1998).
Wengel et al., *Acc. Chem. Res.,* 32:301–310 (1999).
Koshkin et al., *J. Am. Chem. Soc.,* 120:13252–13253 (1998).
Singh et al., *J. Org. Chem.,* 10035–10039 (1998).
Nielsen et al., *Chem. Commun.,* 2645–2646 (1998).
Wengel et al., *Nucleosides Nucleoties,* 28:1365–1370 (1999).
Nielsen et al., *Nucleosides Nucleotides,* 18:701–702 (1999).
Kærno et al., *Chem. Commun.,* 657–658 (1999).
Rajwanshi et al., *J. Chem. Soc., Perkin Trans.,* 1:1407–1414 (1999).
Raunkjær et al., *J. Chem. Soc. Perkin Trans.,* 1:2543–2551 (1999).
Rajwanshi et al., *Chem. Commun.,* 1395–1396 (1999).
Pfundheller et al., *Nucleosides Nucleotides,* 18:2017–2030 (1999).
Rajwanshi et al., *Chem. Commun.,* 2073–2074 (1999).
Nielsen et al., *J. Biomol. Struc. Dyn.,* 17:175–191 (1999).
Nielsen et al., *Bioconjugate Chem.,* 11:228–238 (2000).
Rajwanshi et al., *Angewandte Chemie,* 39:1656–1659 (2000).
Minasov et al., *Biochemistry,* 39:3525 (2000).
Wahlesttedt et al., *Proc. Natl. Acad. Sci. USA,* 97:5633–5638 (2000).
Obika et al., *Tetrahedron Lett.,* 40:6465–6468 (1999).
Obika et al., *Tetrahedron Lett.,* 41:215–219 (1999).
Obika et al., *J. Chem. Soc., Chem. Commun.,* 2423–2424 (1999).
Wang et al., *Bioorg. Med. Chem. Lett.,* 9:1147–1150 (1999).
Obika et al., *Tetrahedron Lett.,* 41:221–224 (1999).
Obika et al., *Bioorg. Med. Chem. Lett.,* 9:515–518 (1999).
Obika et al., *Tetrahedron Lett.,* 39:5401–5405 (1998).
Imanishi et al., *J. Synth. Org. Chem.,* 57:959–980 (1999).
Chemical Abstracts, vol. 70, No. 1, Abstract No. 3737B (1969).
*Monatsch. Chem.,* 99(5):2111–2120 (1968).

* cited by examiner

Illustration of principle

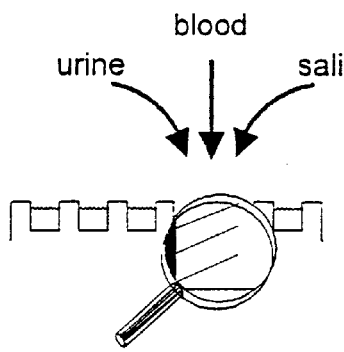

Pipette sample into tube or well with covalently attached LNA catching oligos, lysis buffer, detergent detection probe (LNA) etc.

FIG. IA

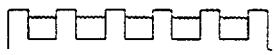

cells lyse, proteins denaturate and nucleic acids are released into solution.

FIG. IB

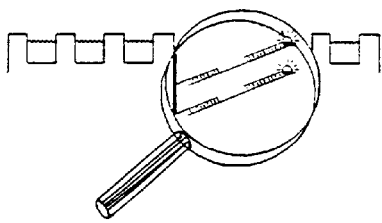

due to the high Tm of LNA's nucleic acid are caught by the catching LNA oligo and hybridize with the detection LNA.

FIG. IC

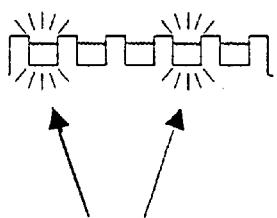

Incubate, wash and add, developing mixture.

develop and read the result of test.

positive samples

FIG. ID

ONE STEP SAMPLE PREPARATION AND DETECTION OF NUCLEIC ACIDS IN COMPLEX BIOLOGICAL SAMPLES

This application claims benefit to Provisional Application No. 60/127,356, filed Apr. 1, 1999.

BACKGROUND OF THE INVENTION

Brief Description of the Relevant Art

Organic solvents such as phenol and chloroform are traditionally used in techniques employed to isolate nucleic acid from prokaryotic and eukaryotic cells or from complex biological samples. Nucleic acid isolations typically begin with an enzymatic digest performed with proteases followed by cell lysis using ionic detergents and then extraction with phenol or a phenol/chloroform combination. The organic and aqueous phases are separated and nucleic acids which have partitioned into the aqueous phase are recovered by precipitation with alcohol. However, phenol or a phenol/chloroform mixture is corrosive to human skin and is considered as hazardous waste which must be carefully handled and properly discarded. Further, the extraction method is time consuming and laborious. Marmur, J. Mol. Biol., 3:208–218 (1961), describes the standard preparative procedure for extraction and purification of intact high molecular weight DNA from prokaryotic organisms using enzymatic treatment, addition of a detergent, and the use of an organic solvent such as phenol or phenol/chloroform. Chirgwin et al., Biochemistry, 18:5294–5299 (1979) described the isolation of intact RNA from tissues enriched in ribonuclease by homogenization in GnSCN and 2-mercaptoethanol followed by ethanol precipitation or by sedimentation through cesium chloride. Further developments of the methods are described by Ausubel et. al in Current Protocols in Molecular Biology, pub. John Wiley & Sons (1998).

Further, the use of chaotropic agents such as guanidine thiocyanate (GnSCN) is widely used to lyse and release nucleic acid from cells into solution, largely due to the fact that the chaotropic salts inhibit nucleases and proteases while at the same time facilitating the lysis of the cells.

Nucleic acid hybridisation is a known and documented method for identifying nucleic acids. Hybridization is based on base pairing of complementary nucleic acid strands. When single stranded nucleic acids are incubated in appropriate buffer solutions, complementary base sequences pair to form double stranded stable molecules. The presence or absence of such pairing may be detected by several different methods well known in the art.

In relation to the present invention a particular interesting technique was described by Dunn & Hassell in Cell, Vol.12, pages 23–36 (1977). Their assay is of the sandwich-type whereby a first hybridisation occurs between a "target" nucleic acid and a "capturing" nucleic acid probe which has been immobilized on a solid support. A second hybridisation then follows where a "signal" nucleic acid probe, typically labelled with a fluorophore, a radioactive isotope or an antigen determinant, hybridises to a different region of the immobilized target nucleic acid. The hybridisation of the signal probe may then be detected by, for example, fluorometry.

Ranki et al. in U.S. Pat. Nos. 4,486,539 and 4,563,419 and EP 0,079,139 describe sandwich-type assays which first require steps to render nucleic acids single stranded and then the single stranded nucleic acids are allowed to hybridise with a nucleic acid affixed to a solid carrier and with a nucleic acid labelled with a radioisotope. Thus, the Ranki et al. assay requires the nucleic acid to be identified or targeted in the assay to be first rendered single stranded.

One approach to dissolving a biological sample in a chaotropic solution and performing molecular hybridisation directly upon the dissolved sample is described by Thompson and Gillespie, "Analytical Biochemistry," 163:281–291 (1987). See also WO 87/06621. Cox et al. have also described the use of GnSCN in methods for conducting nucleic acid hybridisation assays and for isolating nucleic acid from cells (EP-A-0-127-327).

Bresser, Doering and Gillespie, "DNA," 2:243–254 (1983), reported the use of NaI, and Manser and Gefter, Proc. Natl. Acad. Sci. USA, 81:2470–2474 (1984) reported the use of NaSCN to make DNA or mRNA in biological sources available for trapping and immobilization on nitrocellulose membranes in a state which was suitable for molecular hybridisation with DNA or RNA probes.

The use of LNA as capturing-probes and detecting oligos has not been investigated until now. Due to the extraordinary features of LNA, it is possible to obtain efficient hybridisation under conditions where DNA and RNA cannot form stable hybrids e.g. pure water or buffers containing detergents and high concentrations of strong chaotropic agents. Thus, it is possible to perform the steps of catching-hybridisation, detection-hybridisation and cell-lysis in one step. This offers a substantial simplification to previous published methods.

SUMMARY OF THE INVENTION

This invention relates to compositions and assay methods for the hybridisation and extraction of nucleic acids. In particular, this invention relates to compositions and methods to release nucleic acids from cells in complex biological samples or specimens while simultaneously hybridising complementary nucleic acids released during lysis. A crucial component in the invention is LNA which is a novel class of DNA analogues that possess some extraordinary features that make it a prime candidate for improving in vitro DNA diagnostics. The LNA monomers are bi-cyclic compounds structurally very similar to RNA-monomers, see formula I. LNA shares most of the chemical properties of DNA and RNA, it is water-soluble, can be separated by gel electrophoreses, ethanol precipitated etc. Furthermore, LNA oligonucleotides are conveniently synthesised by standard phosphoramidite chemistry. The phosphoramidite chemistry allows chimeric oligos containing both LNA and DNA (or RNA) monomers to be synthesized. Thus, mixed LNA/DNA oligos with a predefined melting temperature ($T_m$) can be prepared. The flexibility of the phosphoramidite synthesis approach furthermore facilitates the easy production of LNAs carrying all commercially available linkers, fluorophores and labelling-molecules available for this standard chemistry. Importantly, introduction of LNA monomers into either DNA or RNA oligos results in unprecedented high thermal stability of duplexes with complementary DNA or RNA while at the same time obeying the Watson-Crick base-pairing rules. In general the thermal stability of heteroduplexes is increased 3–8° C. per LNA-monomer in the duplex. To the best of our knowledge LNA has the highest affinity towards complementary DNA or RNA ever to be reported (Tetrahedron, 54, 3607–3630 (1998)). The thermal stability of LNA/DNA and LNA/RNA heteroduplexes is sufficiently stable to allow efficient hybridisation to occur even in the presence of chaotropic agents such as guanidine thiocyanate (GnSCN).

This invention relates to novel methods for the release of nucleic acids from cells in complex biological samples or specimens to prepare and make available the nucleic acid material present for a hybridisation assay. Novel methods for hybridisation of nucleic acids are also presented. In particular, methods are described for the hybridisation of nucleic acids from a sample suspected of containing a target nucleic acid of interest wherein the sample is combined with a buffer comprising at least one strong chaotropic agent which promotes cell lysis and release of the cellular nucleic acid while at the same time allowing hybridisation with LNA. The extent of hybridisation of the complementary nucleic acid to the target nucleic acid is then determined.

One advantage of these hybridisation methods is that hybridisation may be carried out in one easy step with all reagents pre-combined.

DETAILED DESCRIPTION

This invention relates to a novel method for detecting nucleic acids released from a lysed complex biological mixture containing nucleic acids. The methods of the present invention enable one to readily assay for a nucleic acid suspected of being present in cells, parts of cells or virus, i.e. target nucleic acid(s). Such methods include lysing the cells in a hybridisation medium comprising a strong chaotropic agent, contacting the lysate under hybridisation conditions with a locked nucleic acid (LNA) having a nucleotide sequence substantially complementary to a nucleotide sequence suspected to be present in the cells, and determining the extent of hybridisation.

The "target nucleic acid" means the nucleotide sequence of deoxyribonucleic acid (DNA), ribonucleic acid (RNA) (including ribosomal ribonucleic acid (rRNA), transfer RNA, (tRNA), small nuclear (snRNA), telomerase associated RNA, ribozymes etc.) whose presence is of interest and whose presence or absence is to be detected in the hybridisation assay. The nucleic acid sample of interest will be one which is suspected of containing a particular target nucleic acid, such as a particular gene, gene segment or RNA. Of particular interest is the detection of particular mRNAs which may be of eukaryotic, prokaryotic, Archae or viral origin. Importantly, the invention may assist in the diagnosis of various infectious diseases by assaying for particular sequences known to be associated with a particular micro-organism. The target nucleic acid may be provided in a complex biological mixture of nucleic acid (RNA, DNA and/or rRNA) and non-nucleic acid. The target nucleic acids of primary preference are RNA molecules and, in particular rRNAs such as the 16S or 23S rRNA described in commonly assigned U.S. patent application Ser. No. 08/142,106, which is incorporated by reference herein. If target nucleic acids of choice are double stranded or otherwise have significant secondary and tertiary structure, they may need to be heated prior to hybridisation. In this case, heating may occur prior to or after the introduction of the nucleic acids into the hybridisation medium containing the capturing probe. It may also be desirable in some cases to extract the nucleic acids from the complex biological samples prior to the hybridisation assay to reduce background interference by any methods known in the art.

The hybridisation and extraction methods of the present invention may be applied to a complex biological mixture of nucleic acid (RNA and/or DNA) and non-nucleic acid. Such a complex biological mixture includes a wide range of eukaryotic and prokaryotic cells, including protoplasts; or other biological materials which may harbour target nucleic acids. The methods are thus applicable to tissue culture animal cells, animal cells (e.g., blood, serum, plasma, reticulocytes, lymphocytes, urine, bone marrow tissue, cerebrospinal fluid or any product prepared from blood or lymph) or any type of tissue biopsy (e.g. a muscle biopsy, a liver biopsy, a kidney biopsy, a bladder biopsy, a bone biopsy, a cartilage biopsy, a skin biopsy, a pancreas biopsy, a biopsy of the intestinal tract, a thymus biopsy, a mammae biopsy, an uterus biopsy, a testicular biopsy, an eye biopsy or a brain biopsy, homogenized in lysis buffer), plant cells or other cells sensitive to osmotic shock and cells of bacteria, yeasts, viruses, mycoplasmas, protozoa, rickettsia, fungi and other small microbial cells and the like. The assay and isolation procedures of the present invention are useful, for instance, for detecting non-pathogenic or pathogenic micro-organisms of interest. By detecting specific hybridisation between nucleotide probes of a known source and nucleic acids resident in the biological sample, the presence of the micro-organisms may be established.

Solutions containing high concentrations of guanidine, guanine thiocyanate or certain other chaotropic agents and detergents are capable of effectively lysing prokaryotic and eukaryotic cells while simultaneously allowing specific hybridisation of LNA probes to the released endogenous nucleic acid. The solutions need not contain any other component other than common buffers and detergents to promote lysis and solubilization of cells and nucleic acid hybridisation.

If extraction procedures are employed prior to hybridisation, organic solvents such as phenol and chloroform may be used in techniques employed to isolate nucleic acid. Traditionally, organic solvents, such as phenol or a phenol-chloroform combination are used to extract nucleic acid, using a phase separation (Ausubel et. al in Current Protocols in Molecular Biology, pub. John Wiley & Sons (1998)). These methods may be used effectively with the lysis solutions of the present invention; however, an advantage of the methods of the present invention is that tedious extraction methods are not necessary, thus improving the performance of high throughput assays. Preferably, the lysis buffer/hybridisation medium will contain standard buffers and detergents to promote lysis of cells while still allowing effective hybridisation of LNA probes. A buffer such as sodium citrate, Tris-HCl, PIPES or HEPES, preferably Tris-HCl at a concentration of about 0.05 to 0.5M can be used. The hybridisation medium will preferably also contain about 0.05 to 0.5% of an ionic or non-ionic detergent, such as sodium dodecylsulphate (SDS) or Sarkosyl (Sigma Chemical Co., St. Louis, Mo.) and between 1 and 10 mM EDTA. Other additives may also be included, such as volume exclusion agents which include a variety of polar water-soluble or swellable agents, such as anionic polyacrylate or polymethacrylate, and charged saccharidic polymers, such as dextran sulphate and the like. Specificity or the stringency of hybridisation may be controlled, for instance, by varying the concentration and type of chaotropic agent and the NaCl concentration which is typically between 0 and 1M NaCl, such as 0.1, 0.2, 0.3, 0.4, 0.5, 0.6, 0.7, 0.8, 0.9 or 1.0.

Chaotropic agents which disturb the secondary and tertiary structure of proteins, for example, guanidine salts such as guanidine hydrochloride (GnHCl) and thiocyanate (GnSCN), or urea, lithium chloride and other thiocyanates may be used in combination with detergents and reducing agents such as beta-mercaptoethanol or DTT to dissociate natural occurring nucleic acids and inhibit nucleases. The use of chaotropic agents in the extraction and hybridisation of nucleic acids is described in EP Publication No. 0 127 327, which is incorporated by reference herein.

An LNA substantially complementary to the target nucleic acid will be introduced in the hybridisation process. The term "an LNA substantially complementary to the target nucleic acid" refers to a polynucleotide or oligonucleotide containing at least one LNA monomer and a variable number of naturally occurring nucleotides or their analogues, such as 7-deazaguanosine or inosine, sufficiently complementary to hybridise with the target nucleic acid such that stable and specific binding occurs between the target and the complementary nucleic acid under the hybridisation conditions. Therefore, the LNA sequence need not reflect the exact sequence of the target nucleic acid. For example, a non-complementary nucleotide fragment may be attached to a complementary nucleotide fragment or alternatively, non-complementary bases or longer sequences can be interspersed into the complementary nucleic acid, provided that the complementary nucleic acid sequence has sufficient complementarity with the sequence of the target nucleic acid to hybridise therewith, forming a hybridisation complex and further is capable of immobilizing the target nucleic acid to a solid support as will be described in further detail below. A capturing probe to bind the released nucleic acids can be linked to a group (e.g. biotin, fluorescein, magnetic microparticle etc.). Alternatively, the capturing probe can be permanently bound to a solid phase or particle in advance e.g. by anthraquinone photochemistry (WO 96/31557).

An attractive possibility of the invention is the use of different LNA-oligomers directed against different sequences in the genome which are spotted in an array format and permanently affixed to the surface (Nature Genetics, suppl. vol. 21, January 1999, 1–60 and WO 96/31557). Such an array can subsequently be incubated with the mixture of the lysis buffer/hybridisation medium containing dissolved cells and a number of suitable detection LNA-probes. The lysis and hybridisation would then be allowed to occur, and finally the array would be washed and appropriately developed. The result of such a procedure would be a semi-quantitative assessment of a large number of different target nucleic acids.

As for DNA or RNA the degree of complementarity required for formation of a stable hybridisation complex (duplex) which includes LNA varies with the stringency of the hybridisation medium and/or wash medium. The complementary nucleic acid may be present in a pre-prepared hybridisation medium or introduced at some later point prior to hybridisation.

The hybridisation medium is combined with the biological sample to facilitate lysis of the cells and nucleic acid pairing. Preferably, the volume of biological sample to the volume of the hybridisation medium will be about 1:10.

It is intended and an advantage of the hybridisation methods of the present invention that they be carried out in one step on complex biological samples. However, minor mechanical or other treatments may be considered under certain circumstances. For example, it may be desirable to clarify the lysate before hybridisation such as by slow speed centrifugation or filtration or to extract the nucleic acids before hybridisation as described above.

The hybridisation assay of the present invention can be performed by any method known to those skilled in the art or analogous to immunoassay methodology given the guidelines presented herein. Preferred methods of assay are the sandwich assays and variations thereof and the competition or displacement assay. Hybridization techniques are generally described in "Nucleic Acid Hybridization, A Practical Approach," Ed. Hames, B. D. and Higgins, S. J., IRL Press, 1985; Gall and Pardue (1969), Proc. Natl. Acad. Sci., U.S.A., 63:378–383; and John, Burnsteil and Jones (1969) Nature, 223:582–587. Further improvements in hybridisation techniques will be well known to the person of skill in the art and can readily be applied.

In this invention the capturing LNA-probe is typically attached to a solid surface e.g. the surface of a microtiter tray well or a microbead. Therefore a convenient and very efficient washing procedure can be performed thus opening the possibility for various enzymatically based reactions that may add to the performance of the invention. Most noteworthy is the possibility that the sensitivity of the hybridisation assays may be enhanced through use of a nucleic acid amplification system which multiplies the target nucleic acid being detected. Examples of such systems include the polymerase chain reaction (PCR) system and the ligase chain reaction (LCR) system. Other methods recently described and known to the person of skill in the art are the nucleic acid sequence based amplification (NASBA™, Cangene, Mississauga, Ontario) and Q Beta Replicase systems. PCR is a template dependent DNA polymerase primer extension method of replicating selected sequences of DNA. The method relies upon the use of an excess of specific primers to initiate DNA polymerase replication of specific subsequences of a DNA polynucleotide followed by repeated denaturation and polymerase extension steps. The PCR system is well known in the art (see U.S. Pat. Nos. 4,683,195 and 4,683,202). For additional information regarding PCR methods, see also PCR Protocols: A Guide to Methods and Applications, ed. Innis, Gelland, Shinsky and White, Academic Press, Inc. (1990). Reagents and hardware for conducting PCR are available commercially through Perkin-Elmer/Cetus Instruments of Norwalk, Conn.

LCR, like PCR, uses multiple cycles of alternating temperature to amplify the numbers of a targeted sequence of DNA. LCR, however, does not use individual nucleotides for template extension. Instead, LCR relies upon an excess of oligonucleotides which are complementary to both strands of the target region. Following the denaturation of a double stranded template DNA, the LCR procedure begins with the ligation of two oligonucleotide primers complementary to adjacent regions on one of the target strands. Oligonucleotides complementary to either strand can be joined. After ligation and a second denaturation step, the original template strands and the two newly joined products serve as templates for additional ligation to provide an exponential amplification of the targeted sequences.

This method has been detailed in Genomics, 4:560–569 (1989), which is incorporated herein by reference. As other amplification systems are developed, they may also find use in this invention.

The hybridisation medium and processes of the present invention are uniquely suited to a one-step assay. The medium may be pre-prepared, either commercially or in the laboratory to contain all the necessary components for hybridisation. For instance, in a sandwich assay the medium could comprise a chaotropic agent (e.g. guanidine thiocyanate), desired buffers and detergents, a capturing LNA-probe bound to a solid support such as a microbead, and a detecting nucleic acid which could also be an LNA. This medium then only needs to be combined with the sample containing the target nucleic acid at the time the assay is to be performed. Once hybridisation occurs the hybridisation complex attached to the solid support may be washed and the extent of hybridisation determined.

Sandwich assays are commercially useful hybridisation assays for detecting or isolating nucleic acid sequences.

Such assays utilize a "capturing" nucleic acid covalently immobilized to a solid support and labelled "signal" nucleic acid in solution. The sample will provide the target nucleic acid. The "capturing" nucleic acid and "signal" nucleic acid probe hybridise with the target nucleic acid to form a "sandwich" hybridisation complex. To be effective, the signal nucleic acid is designed so that it cannot hybridise with the capturing nucleic acid, but will hybridise with the target nucleic acid in a different position than the capturing probe.

Virtually any solid surface can be used as a support for hybridisation assays, including metals and plastics. Two types of solid surfaces are generally available, namely:

a) Membranes, polystyrene beads, nylon, Teflon, polystyrene/latex beads, latex beads or any solid support possessing an activated carboxylate, sulfonate, phosphate or similar activatable group are suitable for use as solid surface substratum to which nucleic acids or oligonucleotides can be immobilized.

b) Porous membranes possessing pre-activated surfaces which may be obtained commercially (e.g., Pall Immunodyne Immunoaffinity Membrane, Pall BioSupport Division, East Hills, N.Y., or Immobilon Affinity membranes from Millipore, Bedford, Mass.) and which may be used to immobilize capturing oligonucleotides. Microbeads, including magnetic beads, of polystyrene, teflon, nylon, silica or latex may also be used.

However, use of the generally available surfaces mentioned in a) and b) often creates background problems, especially when complex mixtures of nucleic acids and various other dissolved bio-molecules are analysed by hybridisation. A significant decrease in the background has been obtained when the catching-probe is covalently attached to solid surfaces by the anthraquinone (AQ) based photo-coupling method described in the art (see WO 96/31557). This method allows the covalent attachment of the catching LNA-oligo to the surface of most polymer materials—including various relatively thermostable polymers such as polycarbonate and polyethylene—as well as treated glass surfaces. Thus by use of the AQ photo-coupling method, the capturing LNA-probe can be attached to surfaces of containers that is compatible with present days PCR amplification techniques.

Sequences suitable for capturing or signal nucleic acids for use in hybridisation assays can be obtained from the entire sequence or portions thereof of an organism's genome, from messenger RNA, or from cDNA obtained by reverse transcription of messenger RNA. Methods for obtaining the nucleotide sequence from such obtained sequences are well known in the art (see Ausubel et. al in Current Protocols in Molecular Biology, pub. John Wiley & Sons (1998), and Sambrook et al. in Molecular Cloning, A Laboratory Manual, Cold Spring Habor Laboratory Press, 1989). Furthermore, a number of both public and commercial sequence databases are accessible and can be approached to obtain the relevant sequences.

Once the appropriate sequences are determined, LNA probes are preferably chemically synthesized using commercially available methods and equipment as described in the art (Tetrahedron, 1998, 54, 3607–30.). For example, the solid phase phosphoramidite method can be used to produce short LNA probes. (Caruthers et al., Cold Spring Harbor Symp. Quant. Biol., 47:411–418 (1982), and Adams et al., J. Am. Chem. Soc., 105:661 (1983).

When synthesizing a probe for a specific target, the choice of nucleotide sequence will determine the specificity of the test. For example, by comparing DNA sequences from several virus isolates, one can select a sequence for virus detection that is either type specific or genus specific. Comparisons of DNA regions and sequences can be achieved using commercially available computer programmes.

The determination of the extent of hybridisation may be carried out by any of the methods well-known in the art. If there is no detectable hybridisation, the extent of hybridisation is thus 0. Typically, labelled signal nucleic acids are used to detect hybridisation. Complementary nucleic acids or signal nucleic acids may be labelled by any one of several methods typically used to detect the presence of hybridised polynucleotides. The most common method of detection is the use of ligands which bind to labelled antibodies, fluorophores or chemiluminescent agents. However, probes may also be labelled with $^3H$, $^{125}I$, $^{35}S$ $^{14}C$, $^{33}P$ or $^{32}P$ and subsequently detected by autoradiography. The choice of radioactive isotope depends on research preferences due to ease of synthesis, varying stability, and half lives of the selected isotopes. Other labels include antibodies which can serve as specific binding pair members for a labelled ligand. The choice of label depends on sensitivity required, ease of conjugation with the probe, stability requirements, and available instrumentation.

LNA-probes are typically labelled during synthesis. The flexibility of the phosphoramidite synthesis approach furthermore facilitates the easy production of LNAs carrying all commercially available linkers, fluorophores and labelling-molecules available for this standard chemistry. LNA may also be labelled by enzymatic reactions e.g. by kinasing.

Situations can be envisioned in which the detection probes are DNA or RNA. Such probes can be labelled in various ways depending on the choice of label. Radioactive probes are typically made by using commercially available nucleotides containing the desired radioactive isotope. The radioactive nucleotides can be incorporated into probes by several means such as by nick translation of double-stranded probes; by copying single-stranded M13 plasmids having specific inserts with the Klenow fragment of DNA polymerase in the presence of radioactive dNTP; by transcribing cDNA from RNA templates using reverse transcriptase in the presence of radioactive dNTP; by transcribing RNA from vectors containing SP6 promoters or T7 promoters using SP6 or T7 RNA polymerase in the presence of radioactive rNTP; by tailing the 3' ends of probes with radioactive nucleotides using terminal transferase; or by phosphorylation of the 5' ends of probes using $[^{32}P]$-ATP and polynucleotide kinase.

Non-radioactive probes are often labelled by indirect means. Generally, a ligand molecule is covalently bound to the probe. The ligand then binds to an anti-ligand molecule which is either inherently detectable or covalently bound to a signal system, such as a detectable enzyme, a fluorescent compound, or a chemiluminescent compound. Ligands and antiligands may be varied widely. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

As is the case of DNA, LNA-probes can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, AMPPD ([3-(2'-spiroamantane)4-methoxy4-(3'-phosphoryloxy)-phenyl-1,2-dioxetane]) and 2,3-dihydrophthalazinediones, e.g., luminol.

The amount of labelled probe which is present in the hybridisation medium or extraction solution may vary widely. Generally, substantial excesses of probe over the stoichiometric amount of the target nucleic acid will be employed to enhance the rate of binding of the probe to the target DNA. Treatment with ultrasound by immersion of the reaction vessel into commercially available sonication baths can often accelerate the hybridisation rates.

After hybridisation at a temperature and time period appropriate for the particular hybridisation solution used, the support to which the capturing LNA-probe:target nucleic acid hybridisation complex is attached is introduced into a wash solution typically containing similar reagents (e.g., sodium chloride, buffers, organic solvents and detergent), as provided in the hybridisation solution. These reagents may be at similar concentrations as the hybridisation medium, but often they are at lower concentrations when more stringent washing conditions are desired. The time period for which the support is maintained in the wash solutions may vary from minutes to several hours or more.

Either the hybridisation or the wash medium can be stringent. After appropriate stringent washing, the correct hybridisation complex may now be detected in accordance with the nature of the label.

The probe may be conjugated directly with the label. For example, where the label is raioactive, the probe with associated hybridisation complex substrate is exposed to X-ray film. Where the label is fluorescent, the sample is detected by first irradiating it with light of a particular wavelength. The sample absorbs this light and then emits light of a different wavelength which is picked up by a detector (Physical Biochemistry, Freifelder, D., W. H. Freeman & Co. (1982), pp. 537–542). Where the label is an enzyme, the sample is detected by incubation on an appropriate substrate for the enzyme. The signal generated may be a coloured precipitate, a coloured or fluorescent soluble material, or photons generated by bioluminescence or chemiluminescence. The preferred label for probe assays generates a coloured precipitate to indicate a positive reading, e.g. horseradish peroxidase, alkaline phosphatase, calf intestine alkaline phosphatase, glucose oxidase and beta-galactosidase. For example, alkaline phosphatase will dephosphorylate indoxyl phosphate which will then participate in a reduction reaction to convert tetrazolium salts to highly coloured and insoluble formazans.

Detection of a hybridisation complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridisation complex. For example, where the label is a hapten or antigen, the sample can be detected by using antibodies. In these systems, a signal is generated by attaching fluorescent or enzyme molecules to the antibodies or in some cases, by attachment to a radioactive label. (Tijssen, P., "Practice and Theory of Enzyme Immunoassays," Laboratory Techniques in Biochemistry and Molecular Biology, Burdon, R. H., van Knippenberg, P. H., Eds., Elsevier (1985), pp. 9–20.)

In the present context, the term "label" thus means a group which is detectable either by itself or as a part of an detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are dansyl (5-dimethylamino)-1-naphthalenesulfonyl), DOXYL (N-oxyl4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (trademarks for Biological Detection Systems, Inc.), erytrosine, coumaric acid, umbelliferone, Texas Red, rhodamine, tetramethyl rhodamine, Rox, 7-nitrobenzo-2-oxa-1-diazole (NBD), pyrene, fluorescein, Europium, Ruthenium, Samarium, and other rare earth metals), radio-isotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectroscopy), enzymes (such as peroxidases, alkaline phosphatases, β-galactosidases, and glycose oxidases), antigens, antibodies, haptens (groups which are able to combine with an antibody, but which cannot initiate an immune response by themselves, such as peptides and steroid hormones), carrier systems for cell membrane penetration such as: fatty acid residues, steroid moieties (cholesteryl), vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, Ruthenium, Europium, Cy5, Cy3, etc.

In regard to the isolation of RNA, it has been described (U.S. Pat. No. 5,376,529) that a chaotropic agent, such as a salt of isothiocyanate (e.g. guanidine thiocyanate) does not provide for the complete disruption of protein and nucleic acid interactions, and thus prevents optimal hybridisation. A significant increase in hybridisation was reported to occur when heat is applied to the hybridisation solution containing the chaotropic agent and target nucleic acid. Previously, researchers have attempted to keep hybridisation temperatures low to maintain stability of the reactants. See Cox et al., EP Application No. 84302865.5. However, the significantly increased thermal stability of LNA/DNA and LNA/RNA heteroduplexes makes hybridisation with LNA-probes feasible at elevated temperatures. Thus the present invention provides a method for increasing the sensitivity of ribonucleic acid detection assays and for simplifying the steps of the assays. The processes for conducting nucleic acid hybridisations wherein the target nucleic acid is RNA comprise heating a nucleic acid solution or sample to an elevated temperature e.g. 70–100° C. as described in the art (U.S. Pat. No. 5,376,529). The nucleic acid solution of the present invention will comprise a chaotropic agent, a target nucleic acid, and an LNA substantially complementary to the target nucleic acid of interest. The nucleic acid solution will be heated to fully disrupt the protein and nucleic acid interactions to maximize hybridisation between the LNA and its target.

When very high affinity LNA probes are used, hybridisation may take place even at the increased temperature needed to fully disrupt DNA:DNA and DNA:RNA interactions. The solution is then cooled until the complementary nucleic acid has hybridised with the target nucleic acid to form a hybridisation complex.

These methods are additionally advantageous because they allow for minimal handling of the samples and assay reagents. A ready-to-use reagent solution may be provided, for example, which would contain a chaotropic agent, other appropriate components such as buffers or detergents, a capturing LNA-probe bound to a solid support, and a signal or detection LNA (or nucleic acid), both capable of hybridising with a target nucleic acid. Conveniently, a complex biological sample suspected of harbouring a target nucleic acid can be directly combined with the pre-prepared reagent for hybridisation, thus allowing the hybridisation to occur in one step. The combined solution is heated as described herein and then cooled until hybridisation has occurred. The resulting hybridisation complex is then simply washed to remove unhybridised material, and the extent of hybridisation is determined.

Kits for the extraction of and hybridisation of nucleic acids, e.g. mRNA, are also contemplated. Such kits would contain at least one vial containing an extraction solution or a hybridisation medium which comprises a strong chaotropic agent and a capturing LNA-probe bound to a solid support. Detergents, buffer solutions and additional vials which contain components to detect target nucleic acids may also be included.

When used herein, the terms "LNA" or "capturing LNA-probe" refer to oligomers comprising at least one nucleoside analogue of the general formula I

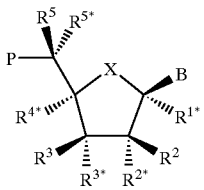

wherein

X is selected from —O—, —S—, —N($R^{N*}$)—, —C$R^6$ ($R^{6*}$)—;

B is selected from nucleobases;

P designates the radical position for an internucleoside linkage to a succeeding monomer, or a 5'-terminal group, such internucleoside linkage or 5'-terminal group optionally including the substituent $R^5$;

$R^3$ or $R^{3*}$ is P* which designates an internucleoside linkage to a preceding monomer, or a 3'-terminal group;

$R^{4*}$ and $R^{2*}$ together designate a biradical consisting of 1–4 groups/atoms selected from —C($R^a R^b$)—, —C($R^a$)=C($R^a$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, heteroaryloxy-carbonyl, heteroaryloxy, heteroarylcarbonyl, amino, mono- and di($C_{1-6}$alkyl)amino, carbamoyl, mono- and di($C_{1-6}$-alkyl)-amino-carbonyl, amino-$C_{1-6}$-alkyl)-aminocarbonyl, mono- and di($C_{1-6}$-alkyl)amino-$C_{1-6}$-alkyl) amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents $R^a$ and $R^b$ together may designate optionally substituted methylene (=CH$_2$, optionally substituted one or two times with substituents as defined as optional substituents for aryl); and each of the substituents $R^{1*}$, $R^2$, $R^3$, $R^{3*}$, $R^5$, $R^{5*}$, $R^6$ and $R^{6*}$ which are present and not involved in P or P*, is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl) amino, carbamoyl, mono- and di($C_{1-6}$alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators photochemically active groups, thermochemically active groups, chelating groups, reporter groups, and ligands (where the latter groups may include a spacer as defined for the substituent B), where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(N$R^N$) — where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof.

When used herein, the term "LNA" (Locked Nucleoside Analogues) refers to the bi-cyclic nucleoside analogues incorporated in the oligomer (general formula I).

In the present context, the term "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4$,$N^4$-ethanocytosine, $N^6$, $N^6$-ethano-2,6-diaminopurine, 5-methylcytosine, 5-($C^3$—$C^6$)-alkynylcytosine, 5-fluorouracil, 5-bromouracil, pseudoisocytosine, 2-hydroxy-5-methyl4-triazolopyridine, isocytosine, isoguanine, inosine and the "non-naturally occurring" nucleobases described in Benner et al., U.S. Pat. No. 5,432, 272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic applications in humans.

When used herein, the term "DNA intercalator" means a group which can intercalate into a DNA or RNA helix, duplex or triplex. Examples of functional parts of DNA intercalators are acridines, anthracene, quinones such as anthraquinone, indole, quinoline, isoquincline, dihydroquinones, anthracyclines, tetracyclines, methylene blue, anthracyclinone, psoralens, coumarins, ethidium-halides, dynemicin, metal complexes such as 1,10-phenanthroline-copper, tris(4,7-diphenyl-1,10-phenanthroline)ruthenium-cobalt-enediynes such as calcheamicin, porphyrins, distamycin, netropcin, viologen, daunomycin. Especially interesting examples are acridines, quinones such as anthraquinone, methylene blue, psoralens, coumarins, and ethidium-halides.

In the present context, the term "photochemically active groups" covers compounds which are able to undergo chemical reactions upon irradiation with light. Illustrative examples of functional groups hereof are quinones, especially 6-methyl-1,4-naphthoquinone, anthraquinone, naphthoquinone, and 1,4-dimethyl-anthraquinone, diazirines, aromatic azides, benzophenones, psoralens, diazo compounds, and diazirino compounds.

In the present context "thermochemically reactive group" is defined as a functional group which is able to undergo thermochemically induced covalent bond formation with other groups. Illustrative examples of functional parts of thermochemically reactive groups are carboxylic acids, carboxylic acid esters such as activated esters, carboxylic acid halides such as acid fluorides, acid chlorides, acid bromide, and acid iodides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, and boronic acid derivatives.

In the present context, the term "chelating group" means a molecule that contains more than one binding site and frequently binds to another molecule, atom or ion through more than one binding site at the same time. Examples of functional parts of chelating groups are iminodiacetic acid, nitrilotriacetic acid, ethylenediamine tetraacetic acid (EDTA), aminophosphonic acid, etc.

In the present context "ligand" means something which binds. Ligands can comprise functional groups such as: aromatic groups (such as benzene, pyridine, naphthalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_1$—$C_{20}$ alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

It will be clear for the person skilled in the art that the above-mentioned specific examples of DNA intercalators, photochemically active groups, thermochemically active groups, chelating groups, reporter groups, and ligands correspond to the "active/functional" part of the groups in question. For the person skilled in the art it is furthermore clear that DNA intercalators, photochemically active groups, thermochemically active groups, chelating groups, reporter groups, and ligands are typically represented in the form M—K—where M is the "active/functional" part of the group in question and where K is a spacer through which the "active/functional" part is attached to the 5- or 6-membered ring. Thus, it should be understood that the group B, in the case where B is selected from DNA intercalators, photochemically active groups, thermochemically active groups, chelating groups, reporter groups, and ligands, has the form M—K—, where M is the "active/functional" part of the DNA intercalator, photochemically active group, thermochemically active group, chelating group, reporter group, and ligand, respectively, and where K is an optional spacer comprising 1–50 atoms, preferably 1–30 atoms, in particular 1–15 atoms, between the 5- or 6-membered ring and the "active/functional" part.

In the present context, the term "spacer" means a thermochemically and photochemically non-active distance-making group which is used to join two or more different moieties of the types defined above. Spacers are selected on the basis of a variety of characteristics including their hydrophobicity, hydrophilicity, molecular flexibility and length (e.g. see Hermanson et. al., "Immobilized Affinity Ligand Techniques", Academic Press, San Diego, Calif. (1992), p. 137-ff). Generally, the length of the spacers is less than or about 400 Å, in some applications preferably less than 100 A. The spacer, thus, comprises a chain of carbon atoms optionally interrupted or terminated with one or more heteroatoms, such as oxygen atoms, nitrogen atoms, and/or sulphur atoms. Thus, the spacer K may comprise one or more amide, ester, amino, ether, and/or thioether functionalities, and optionally aromatic or mono/polyunsaturated hydrocarbons, polyoxyethylene such as polyethylene glycol, oligo/polyamides such as poly-β-alanine, polyglycine, polylysine, and peptides in general, oligosaccharides, oligo/polyphosphates. Moreover the spacer may consist of combined units thereof. The length of the spacer may vary, taking into consideration the desired or necessary positioning and spatial orientation of the "active/functional" part of the group in question in relation to the 5- or 6-membered ring. In particularly interesting embodiments, the spacer includes a chemically cleavable group. Examples of such chemically cleavable groups include disulphide groups cleavable under reductive conditions, peptide fragments cleavable by peptidases, etc.

In one variant, K designates a single bond so that the "active/functional" part of the group in question is attached directly to the 5- or 6-membered ring.

In a preferred embodiment, the substituent B in the general formulae I and II is preferably selected from nucleobases, in particular from adenine, guanine, thymine, cytosine and uracil.

In the oligomers (formula I), P designates the radical position for an internucleoside linkage to a succeeding monomer, or a 5'-terminal group. The first possibility applies when the LNA in question is not the 5'-terminal "monomer", whereas the latter possibility applies when the LNA in question is the 5'-terminal "monomer". It should be understood (which will also be clear from the definition of internucleoside linkage and 5'-terminal group further below)

that such an internucleoside linkage or 5'-terminal group may include the substituent $R^5$ (or equally applicable: the substituent $R^{5*}$) thereby forming a double bond to the group P. (5'-Terminal refers to the position corresponding to the 5' carbon atom of a ribose moiety in a nucleoside.)

On the other hand, an internucleoside linkage to a preceding monomer or a 3'-terminal group (P*) may originate from the positions defined by one of the substituents $R^3$ or $R^{3*}$, preferably from the positions defined by the substituents $R^{3*}$. (3'-Terminal refers to the position corresponding to the 3' carbon atom of a ribose moiety in a nucleoside.)

It should be understood that the orientation of the group P* either as $R^{3*}$ ("normal" configuration) or as $R^3$ (xylo configuration) represents two equally interesting possibilities. It has been found that all-"normal" ($R^{3*}$=P*) oligomers and oligomers with combinations of "normal" LNA monomers and nucleotides (2-deoxynucleotides and/or nucleotides) hybridise strongly (with increasing affinity) to DNA, RNA and other LNA oligomers. It is presently believed that combination of all-xylo LNA oligomers and oligomers with xylo LNA ($R^3$=P*) monomers and, e.g., xylo nucleotides (nucleotides and/or 2-deoxynucleotides) will give rise to comparable hybridisation properties. It has been shown that an oligomer with "normal" configuration ($R^{3*}$=P*) will give rise to an anti-parallel orientation of an LNA oligomer when hybridised (with increasing affinity) to either DNA, RNA or another LNA oligomer. It is thus contemplated that an oligomer with xylo configuration ($R^3$=P*) will give rise to a parallel orientation when hybridised to DNA, RNA or another LNA.

In view of the above, it is contemplated that the combination of "normal" LNAs and xylo-LNAs in one oligomer can give rise to interesting properties as long as these monomers of different type are located in domains, i.e. so that an uninterrupted domain of at least 5, such as at least 10, monomers (e.g. xylo-LNA, xylo-nucleotides, etc. monomers) is followed by an uninterrupted domain of at least 5, e.g. at least 10, monomers of the other type (e.g. "normal" LNA, "normal" nucleotides, etc.), etc. Such chimeric type oligomers may, e.g., be used to capture nucleic acids.

In the present context, the term "monomer" relates to naturally occurring nucleosides, non-naturally occurring nucleosides, PNAs, etc. as well as LNAs. Thus, the term "succeeding monomer" relates to the neighbouring monomer in the 5'-terminal direction and the "preceding monomer" relates to the neighbouring monomer in the 3'-terminal direction. Such succeeding and preceding monomers, seen from the position of an LNA monomer, may be naturally occurring nucleosides or non-naturally occurring nucleosides, or even further LNA monomers.

Consequently, in the present context (as can be derived from the definitions above), the term "oligomer" means an oligonucleotide modified by the incorporation of one or more LNA(s).

In the present context, the orientation of the biradical ($R^{2*}$—$R^{4*}$) is so that the left-hand side represents the substituent with the lowest number and the right-hand side represents the substituent with the highest number, thus, when $R^{2*}$ and $R^{4*}$ together designate a biradical "—O—$CH_2$—", it is understood that the oxygen atom represents $R^{2*}$, thus the oxygen atom is e.g. attached to the position of $R^{2*}$, and the methylene group represents $R^{4*}$.

Considering the numerous interesting possibilities for the structure of the biradical ($R^{2*}$—$R^{4*}$) in LNA(s) incorporated in oligomers, it is believed that the biradical is preferably selected from —$(CR^*R^*)_r$—Y—$(CR^*R^*)_s$—, —$(CR^*R^*)_r$—Y—$(CR^*R^*)_s$—Y—, —Y—$(CR^*R^*)_{r+s}$—Y—, —Y—$(CR^*R^*)_r$—Y—$(CR^*R^*)_s$—, —$(CR^*R^*)_{r+s}$—, —Y—, —Y—Y—, wherein each Y is independently selected from —O—, —S—, —$Si(R^*)_2$—, —$N(R^*)$—, >C=O, —C(=O)—$N(R^*)$—, and —$N(R^*)$—C(=O)—, wherein each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond; and each of r and s is 0–4 with the proviso that the sum r+s is 1–4. Particularly interesting situations are those wherein the biradical is selected from —Y—, —$(CR^*R^*)_{r+s}$—, —$(CR^*R^*)_r$—Y—$(CR^*R^*)_s$—, and —Y—$(CR^*R^*)_{r+s}$—Y—, wherein and each of r and s is 0–3 with the proviso that the sum r+s is 1–4.

Particularly interesting oligomers are those wherein $R^{2*}$ and $R^{4*}$ in at least one LNA in the oligomer together designate a biradical selected from —O—, —S—, —$N(R^*)$—, —$(CR^*R^*)_{r+s+1}$—, —$(CR^*R^*)_r$—O—$(CR^*R^*)_s$—, —$(CR^*R^*)_r$—S—$(CR^*R^*)_s$—, —$(CR^*R^*)_r$—$N(R^*)$—$(CR^*R^*)_s$—, —O—$(CR^*R^*)_{r+s}$—O—, —S—$(CR^*R^*)_{r+s}$—O—, —O—$(CR^*R^*)_{r+s}$—S—, —$N(R^*)$—$(CR^*R^*)_{r+s}$—O—, —O—$(CR^*R^*)_{r+s}$—$N(R^*)$—, —S—$(CR^*R^*)_{r+s}$—S—, —$N(R^*)$—$(CR^*R^*)_{r+s}$—$N(R^*)$—, —$N(R^*)$—$(CR^*R^*)_{r+s}$—S—, and —S—$(CR^*R^*)_{r+s}$—$N(R^*)$—.

It is furthermore preferred that one R* is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen.

In one preferred variant, one group R* in the biradical of at least one LNA is selected from DNA intercalators, photochemically active groups, thermochemically active groups, chelating groups, reporter groups, and ligands (where the latter groups may include a spacer as defined for the substituent B).

Preferably, each of the substituents $R^{1*}$, $R^2$, $R^3$, $R^{3*}$, $R^5$, $R^{5*}$, $R^6$ and $R^{6*}$ of the LNA(s), which are present and not involved in P or P*, is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)-aminocarbonyl, $C_{1-6}$-alkyl-carbonylamino, carbamido, azido, $C_{1-6}$-alkanoyloxy, sulphono, sulphanyl, $C_{1-6}$-alkylthio, DNA intercalators, photochemically active groups, thermochemically active groups, chelating groups, reporter groups, and ligands, and halogen, where two geminal substituents together may designate oxo, and where $R^{N*}$, when present and not involved in a biradical, is selected from hydrogen and $C_{1-4}$-alkyl.

In a preferred variant of the LNAs, X is selected from —O—, —S—, and —$NR^{N*}$—, in particular —O—, and each of the substituents $R^{1*}$, $R^2$, $R^3$, $R^{3*}$, $R^5$, $R^{5*}$, $R^6$ and $R^{6*}$ of the LNA(s), which are present and not involved in P or P*, designates hydrogen.

In an even more preferred variant, X is O, $R^2$ is selected from hydrogen, hydroxy, and optionally substituted $C_{1-6}$alkoxy, one of $R^3$ and $R^{3*}$ is P* and the other is hydrogen, and $R^{1*}$, $R^5$, and $R^{5*}$ designate hydrogen, and, more specifically, the biradical ($R^{2*}$—$R^{4*}$) is selected from —O—, —(CH$_2$)$_{0-1}$—O—(CH$_2$)$_{1-3}$—, —(CH$_2$)$_{0-1}$—S—(CH$_2$)$_{1-3}$—, —(CH$_2$)$_{0-1}$—N(R$^N$)—(CH$_2$)$_{1-3}$—, and —(CH$_2$)$_{2-4}$—, in particular from —O—CH$_2$—, —S—CH$_2$—, and —NR$^H$—CH$_2$—. Generally, with due regard to the results obtained so far, it is preferred that the biradical constituting R$^{2*}$ and R$^{4*}$ forms a two carbon atom bridge, i.e. the biradical forms a five membered ring with the furanose ring (X=O). Particularly interesting are also those oligomers where R$^{2*}$ and R$^{4*}$ of an incorporated LNA of formula I together designate a biradical selected from —O—CH$_2$—, —S—CH$_2$—, and —NR$^H$—CH$_2$—; X is O, B designates a nucleobase selected from adenine, guanine, thymine, cytosine and uracil; R$^2$ is hydrogen, one of R$^3$ or R$^{3*}$ designates P* and the other is hydrogen, and R$^{1*}$, R$^3$, R$^5$, and R$^{5*}$ designate hydrogen.

In these embodiments, it is furthermore preferred that at least one LNA incorporated in an oligomer includes a nucleobase (substituent B) selected from adenine and guanine. In particular, it is preferred that an oligomer having LNA incorporated therein includes at least one nucleobase selected from thymine, uracil and cytosine and at least one nucleobase selected from adenine and guanine. For LNA monomers, it is especially preferred that the nucleobase is selected from adenine and guanine.

Within a variant of these interesting embodiments, all monomers of a oligonucleotide are LNA monomers.

As it will be evident from the general formula I (LNA(s) in an oligomer) and the definitions associated therewith, there may be one or several asymmetric carbon atoms present in the oligomers depending on the nature of the substituents and possible biradicals, cf. below.

In one variant, R$^{3*}$ designates P*. In another variant, R$^3$ designates P*, and in a third variant, some R$^{3*}$ designates P* in some LNAs and R$^3$ designates P* in other LNAs within an oligomer.

The oligomers typically comprise 1–10000 LNA(s) of the general formula I and 0–10000 nucleosides selected from naturally occurring nucleosides and nucleoside analogues. The sum of the number of nucleosides and the number of LNA(s) is at least 2, preferably at least 3, in particular at least 5, especially at least 7, such as in the range of 2–15000, preferably in the range of 2–100, such as 3–100, in particular in the range of 2–50, such as 3–50 or 5–50 or 7–50.

In the present context, the term "nucleoside" means a glycoside of a heterocyclic base. The term "nucleoside" is used broadly as to include non-naturally occurring nucleosides, naturally occurring nucleosides as well as other nucleoside analogues. Illustrative examples of nucleosides are ribonucleosides comprising a ribose moiety as well as deoxyribonuclesides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

When considering the definitions and the known nucleosides (naturally occurring and nonnaturally occurring) and nucleoside analogues (including known bi- and tricyclic analogues), it is clear that an oligomer may comprise one or more LNA(s) (which may be identical or different both with respect to the selection of substituent and with respect to selection of biradical) and one or more nucleosides and/or nucleoside analogues. In the present context "oligonucleotide" means a successive chain of nucleosides connected via internucleoside linkages; however, it should be understood that a nucleobase in one or more nucleotide units (monomers) in an oligomer (oligonucleotide) may have been modified with a substituent B as defined above.

As mentioned above, the LNA(s) of an oligomer is/are connected with other monomers via an internucleoside linkage. In the present context, the term "internucleoside linkage" means a linkage consisting of 2 to 4, preferably 3, groups/atoms selected from —CH$_2$—, —O—, —S—, —NR$^H$—, >C=O, >C=NR$^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where R$^H$ is selected form hydrogen and C$_{1-4}$-alkyl, and R" is selected from C$_{1-6}$-alkyl and phenyl. Illustrative examples of such internucleoside linkages are —CH$_2$—CH$_2$—CH$_2$—, —CH$_2$—CO—CH$_2$—, —CH$_2$—CHOH—CH$_2$—, —O—CH$_2$—O—, —O—CH$_2$—CH$_2$—, —O—CH$_2$—CH= (including R$^5$ when used as a linkage to a succeeding monomer), —CH$_2$—CH$_2$—O—, —NR$^H$—CH$_2$—CH$_2$—, —CH$_2$—CH$_2$—NR$^H$—, —CH$_2$—NR$^H$—CH$_2$—, —O—CH$_2$—CH$_2$—NR$^H$—, —NR$^H$—CO—O—, —NR$^H$—CO—NR$^H$—, —NR$^H$—CS—NR$^H$—, —NR$^H$—C(=NR$^H$)—NR$^H$—, —NR$^H$—CO—CH$_2$—NR$^H$—, —O—CO—O—, —O—CO—CH$_2$—O—, —O—CH$_2$—CO—O—, —CH$_2$—CO—NR$^H$—, —O—CO—NR$^H$—, —NR$^H$—CO—CH$_2$—, —O—CH$_2$—CO—NR$^H$—, —O—CH$_2$—NR$^H$—, —CH=N—O—, —CH$_2$—NR$^H$—O—, —CH$_2$—O—N= (including R$^5$ when used as a linkage to a succeeding monomer), —CH$_2$—O—NR$^H$—, —CO—NR$^H$—CH$_2$—, —CH$_2$—NR$^H$—O—, —CH$_2$—NR$^H$—CO—, —O—NR$^H$—CH$_2$—, —O—NR$^H$—, —O—CH$_2$—S—, —S—CH$_2$—O—, —CH$_2$—CH$_2$—S—, —O—CH$_2$—CH$_2$—S—, —S—CH$_2$—CH= (including R$^5$ when used as a linkage to a succeeding monomer), —S—CH$_2$—CH$_2$—, —S—CH$_2$—CH$_2$—O—, —S—CH$_2$—CH$_2$—S—, —CH$_2$—S—CH$_2$—, —CH$_2$—SO—CH$_2$—, —CH$_2$—SO$_2$—CH$_2$—, —O—SO—O—, —O—S(O)$_2$—O—, —O—S(O)$_2$—CH$_2$—, —O—S(O)$_2$—NR$^H$—, —NR$^H$—S(O)$_2$—CH$_2$—, —O—S(O)$_2$—CH$_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—NR$^H$—, —NR$^H$—P(O)$_2$—O—, —O—P(O,NR$^H$)—O—, —CH$_2$—P(O)$_2$—O—, —O—P(O)$_2$—CH$_2$—, and —O—Si(R")$_2$—O—; among which —CH$_2$—CO—NR$^H$—, —CH$_2$—NR$^H$—O—, —S—CH$_2$—O—, —O—P(O)$_2$—O—, —O—P(O,S)—O—, —O—P(S)$_2$—O—, —NR$^H$—P(O)$_2$—O—, —O—P(O,NR$^H$)—O—, —O—PO(R")—O—, —O—PO(CH$_3$)—O—, and —O—PO(NHR$^N$)—O—, where R$^H$ is selected from hydrogen and C$_{1-4}$-alkyl, and R" is selected from C$_{1-6}$-alkyl and phenyl, are especially preferred. Further illustrative examples are given in Mesmaeker et. al., Current Opinion in Structural Biology 1995, 5, 343–355. The left-hand side of the internucleoside linkage is bound to the 5-membered ring as substituent P*, whereas the right-hand side is bound to the 5'-position of a preceding monomer.

It is also clear from the above that the group P may also designate a 5'-terminal group in the case where the LNA in question is the 5'-terminal monomer. Examples of such 5'-terminal groups are hydrogen, hydroxy, optionally substituted C$_{1-6}$-alkyl, optionally substituted C$_{1-6}$-alkoxy, optionally substituted C$_{1-6}$-alkylcarbonyloxy, optionally substituted aryloxy, monophosphate, diphosphate, triphosphate, and —W—A', wherein W is selected from —O—, —S—, and —N(R$^H$) where R$^H$ is selected from hydrogen and C$_{1-6}$alkyl, and where A' is selected from DNA intercalators, photochemically active groups, thermochemically active groups, chelating groups, reporter groups, and ligands (where the latter groups may include a spacer as defined for the substituent B).

In the present description and claims, the terms "monophosphate", "diphosphate", and "triphosphate" mean groups of the formula: —O—P(O)$_2$—O$^-$, —O—P(O)$_2$—O—P(O)$_2$—O$^-$, and —O—P(O)$_2$—O—P(O)$_2$—O—P(O)$_2$—O$^-$, respectively.

In a particularly interesting embodiment, the group P designates a 5'-terminal group selected from monophosphate, diphosphate and triphosphate. Especially the triphosphate variant is interesting as a substrate for nucleic acid polymerases.

Analogously, the group P* may designate a 3'-terminal group in the case where the LNA in question is the 3'-terminal monomer. Examples of such 3'-terminal groups are hydrogen, hydroxy, optionally substituted C$_{1-6}$-alkoxy, optionally substituted C$_{1-6}$-alkylcarbonyloxy, optionally substituted aryloxy, and —W—A', wherein W is selected from —O—, —S—, and —N(R$^H$)—where R$^H$ is selected from hydrogen and C$_{1-6}$-alkyl, and where A' is selected from DNA intercalators, photochemically active groups, thermochemically active groups, chelating groups, reporter groups, and ligands (where the latter groups may include a spacer as defined for the substituent B).

In a preferred variant of the LNAs, the oligomer has the following formula V:

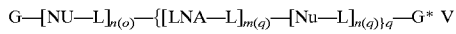

G—[NU—L]$_{n(o)}$—{[LNA—L]$_{m(q)}$—[Nu—L]$_{n(q)}$}$_q$—G* V wherein q is 1–50;

each of n(0), . . . , n(q) is independently 0–10000;

each of m(1), . . . , m(q) is independently 1–10000;

with the proviso that the sum of n(0), . . . , n(q) and m(1), . . . , m(q) is 2–15000;

G designates a 5'-terminal group;

each Nu independently designates a nucleoside selected from naturally occurring nucleosides and nucleoside analogues;

each LNA independently designates a nucleoside analogue;

each L independently designates an internucleoside linkage between two groups selected from Nu and LNA, or L together with G* designates a 3'-terminal group; and each LNA-L independently designates a nucleoside analogue of the general formula I as defined above.

Within this variant, as well as generally, the LNAs preferably include different nucleobases, in particular both nucleobases selected from thymine, cytosine and uracil and nucleobases selected from adenine and guanine.

The oligomers are also intended to cover chimeric oligomers. The term "chimeric oligomers" means two or more oligomers with monomers of different origin joined either directly or via a spacer. Illustrative examples of such oligomers which can be combined are peptides, PNA-oligomers, oligomers containing LNAs, and oligonucleotide oligomers. The combination of an oligomer having xylo-LNA (R$^3$=P*) domain(s) and "normal" LNA (R$^{3*}$=P*) domain(s) might be construed as an example of a chimeric oligomer as the various domains may have different affinity and specificity profiles.

Generally, the oligomers have surprisingly good hybridisation properties with respect to affinity and specificity. Thus, the oligomers comprise at least one nucleoside analogue which imparts to the oligomer a T$_m$ with a complementary DNA oligonucleotide which is at least 2.5° C. higher, preferably at least 3.5° C. higher, in particular at least 4.0° C. higher, especially at least 5.0° C. higher, than that of the corresponding unmodified reference oligonucleotide which does not comprise any nucleoside analogue. In particular, the T$_m$ of the oligomer is at least 2.5×N° C. higher, preferably at least 3.5×N° C. higher, in particular at least 4.0×N° C. higher, especially at least 5.0×N ° C. higher, where N is the number of nucleoside analogues.

In the case of hybridisation with a complementary RNA oligonucleotide, the at least one nucleoside analogue imparts to the oligomer a T$_m$ with the complementary DNA oligonucleotide which is at least 4.0° C. higher, preferably at least 5.0° C. higher, in particular at least 6.0° C. higher, especially at least 7.0° C. higher, than that of the corresponding un-modified reference oligonucleotide which does not comprise any nucleoside analogue. In particular, the T$_m$ of the oligomer is at least 4.0×N° C. higher, preferably at least 5.0×N° C. higher, in particular at least 6.0×N° C. higher, especially at least 7.0×N° C. higher, where N is the number of nucleoside analogues.

The term "corresponding unmodified reference oligonucleotide" is intended to mean an oligonucleotide solely consisting of naturally occurring nucleotides which represents the same nucleobases in the same absolute order (and the same orientation).

The T$_m$ is measured under one of the following conditions:

a) 10 mM Na$_2$HPO$_4$, pH 7.0, 100 mM NaCl, 0.1 mM EDTA;

b) 10 mM Na$_2$HPO$_4$ pH 7.0, 0.1 mM EDTA; or c) 3 M tetramethylammoniumchloride (TMAC), 10 mM Na$_2$HPO$_4$, pH 7.0, 0.1 mM EDTA;

preferably under conditions a), at equimolar amounts (typically 1.0 µM) of the oligomer and the complementary DNA oligonucleotide.

The oligomer is preferably as defined above, where the at least one nucleoside analogue has the formula I where B is a nucleobase. Especially interesting are the cases where at least one nucleoside analogue includes a nucleobase selected from adenine and guanine.

Furthermore, with respect to specificity and affinity, the oligomer, when hybridised with a partially complementary DNA oligonucleotide, or a partially complementary RNA oligonucleotide, having one or more mismatches with said oligomer, should exhibit a reduction in T$_m$, as a result of said mismatches, which is equal to or greater than the reduction which would be observed with the corresponding unmodified reference oligonucleotide which does not comprise any nucleoside analogues. Also, the oligomer should have substantially the same sensitivity of T$_m$ to the ionic strength of the hybridisation buffer as that of the corresponding unmodified reference oligonucleotide.

Oligomers defined herein are typically at least 1% modified, such as at least 2% modified, e.g. 3% modified, 4% modified, 5% modified, 6% modified, 7% modified, 8% modified, or 9% modified, at least 10% modified, such as at least 11% modified, e.g. 12% modified, 13% modified, 14% modified, or 15% modified, at least 20% modified, such as at least 30% modified, at least 50% modified, e.g. 70% modified, and in some interesting applications 100% modified.

The oligomers preferably have substantially higher 3'-exonucleolytic stability than the corresponding unmodified reference oligonucleotide.

It should be understood that oligomers (wherein LNAs are incorporated) and LNAs as such include possible salts thereof, of which pharmaceutically acceptable salts are especially relevant. Salts include acid addition salts and basic salts. Examples of acid addition salts are hydrochloride salts, sodium salts, calcium salts, potassium salts, etc.. Examples of basic salts are salts where the (remaining) counter ion is selected from alkali metals, such as sodium and potassium, alkaline earth metals, such as calcium, and ammonium ions ($^+N(R^g)_3R^h$, where each of $R^g$ and $R^h$ independently designates optionally substituted $C_{1-6}$-alkyl, optionally substituted $C_{2-6}$-alkenyl, optionally substituted aryl, or optionally substituted heteroaryl). Pharmaceutically acceptable salts are, e.g., those described in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology. Thus, the term "an acid addition salt or a basic salt thereof" used herein is intended to comprise such salts. Furthermore, the oligomers and LNAs as well as any intermediates or starting materials therefor may also be present in hydrate form.

Figure 1:
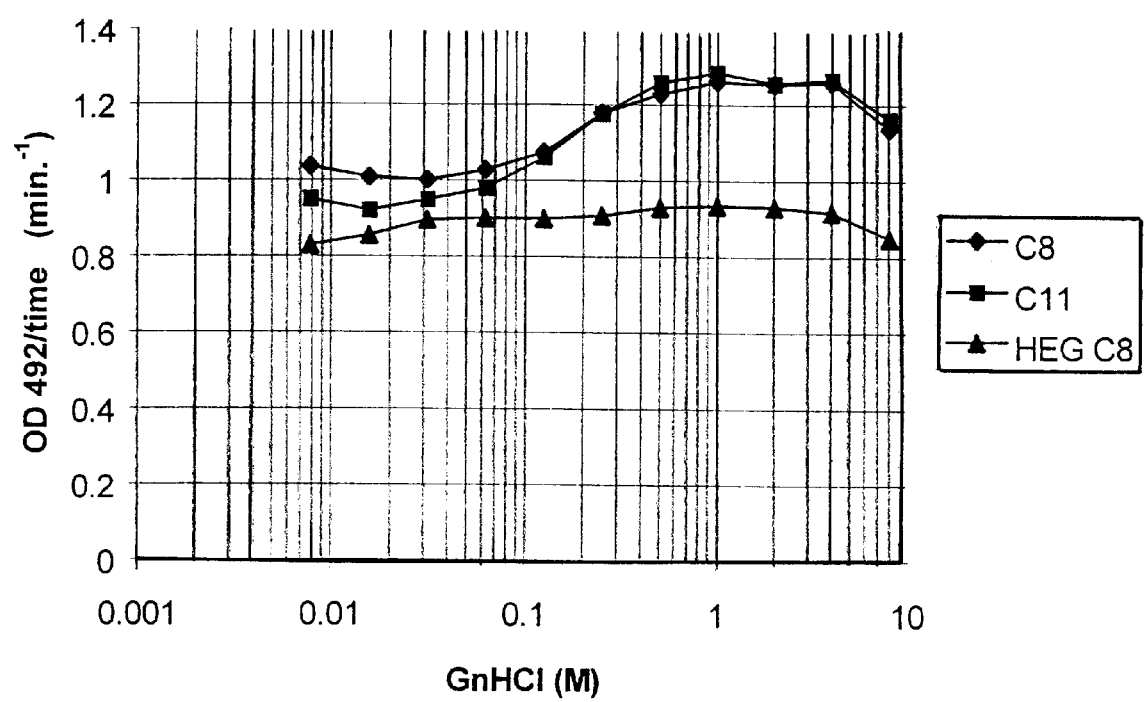
FIG. 1.

Illustrates one embodiment of the invention.

FIG. 1-1.

Hybridization experiment performed with 3 different LNA modified oligos (see table 1-1) covalently immobilized to the wells of a microtiter-plate probe and a complementary target DNA oligo. The hybridisations were performed at variable concentrations of guanidine-hydrochloride (GnHCl) as indicated.

FIG. 2-1.

Competition assay illustrating the specificity of the LNA hybridisation performed at variable concentrations of guanidine hydrochloride. The amount of matching wild type oligo is kept constant at a concentration of 0.5 nM while the concentration of the competing (one base mismatching mutant oligo) is varied from 0.1 nM to 0.3 $\mu$M. The arrow indicates equimolar amounts of target and competing oligo. Also indicated is the hybridisation performance obtained in hybridisation buffers containing from 0 to 8 M guanidine hydrochloride (GnHCl).

FIG. 2-2.

Competition assay illustrating the specificity of the LNA hybridisation performed at variable concentrations of guanidine hydrochloride. The amount of matching mutant type oligo is kept constant at a concentration of 5 nM while the concentration of the competing (one base mismatching wild type oligo) is varied from 0.1 nM to 0.3 $\mu$M. The arrow indicates equimolar amounts of target and competing oligo. Also indicated is the hybridisation performance obtained in hybridisation buffers containing from 0 to 8 M guanidine hydrochloride (GnHCl).

FIG. 3-1.

LNA hybridisation experiment performed with 2 different LNA modified oligos (see table 3-1) covalently immobilized to the wells of a microtiter-plate probe and two complementary target DNA oligos. The hybridisations were performed at variable concentrations of guanidine thiocyanate (GnSCN) and in buffers based on either sodium citrate or phosphate as indicated.

FIG. 4-1.

Competition assay illustrating the specificity of the hybridisation performed phosphate based buffers and variable of guanidine thiocyanate (GnSCN). The amount of matching wild type oligo is kept constant at a concentration of 0.5 nM while the concentration of the competing (one base mismatching mutant oligo) is varied from 0.1 nM to 0.3 $\mu$M. The arrow indicates equimolar amounts of target and competing oligo. Also indicated is the hybridisation performance obtained in hybridisation buffers containing from 0 to 4 M GnSCN.

FIG. 4-2.

Competition assay illustrating the specificity of the hybridisation performed phosphate based buffers and variable of guanidine thiocyanate (GnSCN). The amount of matching mutant type oligo is kept constant at a concentration of 5 nM while the concentration of the competing (one base mismatching wild type oligo) is varied from 0.1 nM to 0.3 $\mu$M.

The arrow indicates equimolar amounts of target and competing oligo. Also indicated is the hybridisation performance obtained in hybridisation buffers containing from 0 to 4 M GnSCN.

FIG. 4-3.

Competition assay illustrating the specificity of the hybridisation performed sodium citrate based buffers and variable of guanidine thiocyanate (GnSCN). The amount of matching wild type oligo is kept constant at a concentration of 0.5 nM while the concentration of the competing (one base mismatching mutant oligo) is varied from 0.1 nM to 0.3 $\mu$M. The arrow indicates equimolar amounts of target and competing oligo. Also indicated is the hybridisation performance obtained in hybridisation buffers containing from 0 to 4 M guanidine thiocyanate (GnSCN).

FIG. 44.

Competition assay illustrating the specificity of the hybridisation performed sodium citrate based buffers and variable of guanidine thiocyanate (GnSCN). The amount of matching mutant type oligo is kept constant at a concentration of 5 nM while the concentration of the competing (one base mismatching wild type oligo) is varied from 0.1 nM to 0.3 $\mu$M. The arrow indicates equimolar amounts of target and competing oligo. Also indicated is the hybridisation performance obtained in in hybridisation buffers containing from 0 to 4 M GnSCN.

FIG. 6-1.

Detection of single nucleotide polymorphism. Biotinylated PCR amplicons from three human cell lines (HCV29, T112C1 and T112D1) and a plasmid were generated. All three human cell lines are wild type (G-allele) with respect to the ApoB3500 mutation. The "A-allele" plasmid contains the ApoB R3500Q mutation (a G−>A transition at amino acid 3500 (arg−>gln)). Each sample was tested against wild type (C8) or mutant (T8) specific LNA capture probes. Black bars: wild type. Light bars: mutant type.

FIG. 7-1.

Detection of plasmid DNA in bacterial cell lysates. Three different bacterial strains (see Table 7-1) were lysed and hybridised to either the C11 or the T11capture probes (see table 7-2) covalently immobilized to the wells of a microtiter-plate. The hybridisations were performed in a hybridisation buffer containing 2 M guanidine thiocyanate. NF1815 cells contain no plasmid, TOP10/pCR cells contain the pCR®2.1-TOPO plasmid without the ApoB sequence and TOP10/pApoBwt cells contain the ApoB3500 wild-type sequence inserted into the pCR®2.1-TOPO plasmid.

EXAMPLE 1
GnHCl Allows and Enhances LNA Hybridization in Phosphate Buffer

To study the effect that strong chaotrophic agents such as guanidine hydrochloride (GnHCl) exert on the hybridisation, the following experiment was carried out.

LNA modified oligos (see table 1-1) carrying a 5' anthraquinone were covalently immobilized to the wells of a microtiter-plate by UV irradiation and used as capture probes in a hybridisation assay with a complementary target DNA oligo. The hybrid was detected by including a 5' biotinylated DNA detection probe in the hybridisation mixture.

TABLE 1-1

Oligonucleotides studied

| Name | EQ number | SEQ ID NO | Sequence | Characteristics |
|---|---|---|---|---|
| C8 | EQ-3133 | 4 | 5'-AQ-tac atg tta tgc ttt GAC$^{met}$C$^{met}$GT GTg-3' | 5' anthraquinone modified LNA |
| C11 | EQ-3131 | 5 | 5'-AQ-tac atg tta tgc ttt AAG AC$^{met}$C$^{met}$ GTG TGc-3' | 5' anthraquinone modified LNA |
| HEG C 8 | EQ-3108 | 6 | 5'-AQ-HEG-AGA C$^{met}$CG TGt-3' | 5' hexaethylene glycol LNA |
| Wild type target molecule | EQ-3185 | 7 | 5'ttg aat tcc aag agc aca cgg tct tca gtg aag ctg cag ggc act tcc aa 3' | Wildtype, sense g/c pos. 9756 (50-mer) |
| Detection probe | EQ-3246 | 8 | 5'-biotin-ttg gaa gtg ccc tgc agc tt-3' | 5' biotinylated DNA |

Note:
LNA monomers are indicated in uppercase letters, DNA monomers are indicated in lowercase letters. C$^{met}$ indicates that the monomer is 5-methyl cytosine LNA. 5'-AQ indicates that the oligo carries a 5'anthraquinone (AQ) and a C3 linker, the composition is AQ—CONH—(CH$_2$)$_3$-oligo. 5'-AQ—HEG indicates that the 5'end of the oligo is: AQ—CONH—(CH$_2$)$_3$—PO$_4$—((CH$_2$)$_2$O)$_5$—(CH$_2$)$_2$-oligo. 5'-biotin indicates that the 5'end of the oligo is: Biotin-(CH$_2$)$_4$—CONH—(CH$_2$)$_6$-oligo.

Immobilizing ApoB Capture Probes

Anthraquinone LNA capture probes (either C8, C11 or HEG C 8 —see table 1-1) were dissolved in 0.2 M NaCl at a concentration of 0.1 µM. 100 µL of the oligos were added to each of the wells of the microtiter-plate (C96 polysorp; Nalge Nunc International, Roskilde, Denmark), and exposed for 15 min. to soft UV light (approximately 350 nm) in a ULS-20-2 illuminator (UV-Lights Systems, Denmark) at maximal 35° C. The illuminator is equipped with 28 Philips Cleo Compact 25W-S light bulbs (14 located above and 14 located below the glass plate sample holder); only the upper bulbs were lit.

After incubation the wells were washed with first 300 µL of 0.4 M NaOH with 0.25% Tween 20 (Riedel-de Haen, Seeize, Germany) and then three times with 300 µL of deionized water.

Hybridization With Target and Detection Probe

Wild type (WT) target molecules (0.3 µM, EQ3185, SEQ ID NO 7) were added to micro-titer-plate wells coated with either C8, C11 or HEG C8 capture probe. The concentration of GnHCl in the hybridisation mixture was varied in twofold "dilutions" as described below. The resulting concentrations of GnHCl were: 0.0078, 0.016, 0.032, 0.063, 0.13, 0.25, 0.5, 1, 2, 4 and 8 M.

Hybridization buffers were constructed by dissolving solid GnHCl to a final concentration of 8 M in 50 mM phosphate buffer, pH 7, with 0.1% Tween 20. Buffers with lower concentrations of GnHCl were the constructed by diluting the buffer containing 8 M GnHCl with a similar buffer containing 0 M GnHCl. 100 µL of hybridisation mix were added per microtiter-plate well. The capture and target oligos were allowed to hybridise for half an hour at 37° C. Then the wells were washed five times with 300 µL of 1×SSC with 0.1% Tween 20 (1×SSC is: 150 mM NaCl, 15 mM sodium citrate). Then, 100 µL of 0.12 µM detection probe (EQ-3246, SEQ ID NO 8) dissolved in 1×SSC with 0.1% Tween 20 were added and allowed to hybridise for half an hour at 37° C. Finally the microtiter-plate was washed three times with 1×SSC with 0.1% Tween 20.

The hybrids were detected by binding streptavidin-horseradish peroxidase (strA-HRP) to the biotinylated detection probe. The strA-HRP (Pierce, Rockford, Ill., U.S.A. Cat. no. 21126) was dissolved in 1×SSC with 0.1% Tween 20 at a concentration of 1 µg/mL. 100 µL was added per well and incubated 15 min. Then the plate was washed three times with 1×SSC; 0.1% Tween 20 and the signal developed in the OPD-assay.

OPD-assay

A master-mix containing: 6 mL of 0.1 M citrate buffer pH=5.0, two 2 mg ortho-phenylenediamine (OPD) tablets (Kem-En-Tech, Copenhagen, Denmark) and 2.5µL of 30% H$_2$O$_2$ was prepared. 100 µL of the master-mix is added to each reaction chamber and is left to incubate for one to 30 min. depending on enzyme activity. The assay is stopped with 100 µL of 0.5 M H$_2$SO$_4$ and the optical density is measured at λ=492 nm with an ELISA-reader.

Results

The results are shown in FIG. 1-1.

Conclusion

From the experiment it is concluded that it is possible to hybridise with good efficiency in buffers containing GnHCl. Surprisingly, it is observed that the hybridisation signal is enhanced with increasing concentrations of GnHCl. Even at very high (8 M) GnHCl concentrations, a high hybridisation signal is obtained. Actually, in the case of capture oligos with a DNA-linker (C8 (EQ-, SEQ ID NO 4) and C11 (EQ-3131, SEQ ID NO 5)) the hybridisation signal increases as a function of GnHCl concentration starting its effect at about 0.1 M and having its optimum from about 0.5 M to 5 M enhancing the hybridisation signal some 30%. Hybridization to capture probes immobilized to the surface of the microtiter-plate via the hexaethylene glycol linker (HEG C 8 (EQ-3108, SEQ ID NO 6)) appears less affected.

EXAMPLE 2.

Hybridization in GnHCl is Specific (Competition Experiment)

To study if hybridisation in buffers containing strong chaotrophic agents such as guanidine hydrochloride (GnHCl) can be performed at sufficiently high stringency to allow single-base discrimination, the following experiment was carried out.

LNA modified oligos (see table 2-1) carrying a 5' anthraquinone were covalently immobilized to the wells of a microtiter-plate by UV irradiation and used as capture probes in a hybridisation assay with a complementary target DNA oligo. The hybrid was detected by including a 5' biotinylated DNA detection probe in the hybridisation mixture.

TABLE 2-1

Oligonucleotides studied

| Name | EQ number | SEQ ID NO | Sequence | Characteristics |
|---|---|---|---|---|
| C8 | EQ-3133 | 4 | 5'-AQ-tac atg tta tgc ttt GAC$^{met}$C$^{met}$GT GTg-3' | 5' anthraquinone modified LNA |
| T8 | EQ-3134 | 9 | 5'-AQ-tac atg tta tgc ttt GAC$^{met}$TGT GTg-3' | 5' anthraquinone modified LNA |
| Wild type target molecule | EQ-3185 | 7 | 5'ttg aat tcc aag agc aca cgg tct tca gtg aag ctg cag ggc act tcc aa 3' | Wildtype, sense g/c pos. 9756 (50-mer) |
| Mutation type target molecule | EQ-3187 | 10 | 5'ttg aat tcc aag agc aca cag tct tca gtg aag ctg cag ggc act tcc aa 3' | Sense a/t pos. 9756 (50-mer) |
| Detection probe | EQ-3246 | 8 | 5'-biotin-ttg gaa gtg ccc tgc agc tt-3' | 5' biotinylated DNA |

Note:
LNA monomers are indicated in uppercase letters, DNA monomers are indicated in lowercase letters. C$^{met}$ indicates that the monomer is 5-methyl cytosine LNA. 5'-AQ indicates that the oligo carries a 5'anthraquinone (AQ) and a C3 linker, the composition is AQ—CONH—(CH$_2$)$_3$-oligo. 5'-biotin indicates that the 5'end of the oligo is: Biotin-(CH$_2$)$_4$—CONH—(CH$_2$)$_6$-oligo.

Immobilizing ApoB Capture Probes

Anthraquinone LNA capture probes (either C8 or T8—see table 2-1) were dissolved in 0.2 M NaCl at a concentration of 0.1 µM. 100 µL of the oligos were added to each of the wells of the microtiter-plate (C96 polysorp; Nalge Nunc International, Roskilde, Denmark), and exposed for 15 min. to soft UV light (approximately 350 nm) in a ULS-20-2 illuminator (UV-Lights Systems, Denmark) at maximal 35° C. The illuminator is equipped with 28 Philips Cleo Compact 25W-S light bulbs (14 located above and 14 located below the glass plate sample holder); only the upper bulbs were lit.

After incubation the wells were washed with first 300 µL of 0.4 M NaOH with 0.25% Tween 20 (Riedel-de Haen, Seeize, Germany) and then three times with 300 µL of deionized water.

Hybridization With Wild Type Target Molecule (EQ-3185) and Mutation Type Target Molecule (EQ-3187)

To wells coated with C8 capture probe (EQ 3133, SEQ ID NO 4) wild type target molecule (EQ3185, SEQ ID NO 7) was added in a constant low concentration (0.0005 µM) while the amount of the competing single base mismatching mutation type target molecule (EQ3187, SEQ ID NO 10) was varied in a five-fold "dilution series". The resulting concentrations of the mutation type target molecule were: 0.0001, 0.0005, 0.0025, 0.012, 0.06 and 0.30 µM.

To chambers coated with T8 capture probe (EQ3134, SEQ ID NO 9) mutation type target molecule was added in a constant low concentration (0.005 µM) while the amount of the competing single base mismatching wild type target molecule (EQ3185, SEQ ID NO 7) was varied in a five-fold "dilution series". The resulting concentrations of the wild type target molecule were: 0.0001, 0.0005, 0.0025, 0.012, 0.06 and 0.30 µM.

Hybridization buffers were constructed by dissolving solid GnHCl to a final concentration of 8 M in 50 µM phosphate buffer, pH 7, with 0.1% Tween 20. Buffers with lower concentrations of GnHCl were then constructed by diluting the buffer containing 8 M GnHCl with similar buffer containing 0 M GnHCl.

100 µL of hybridisation mix were added per microtiter-plate well. The capture and target oligos were allowed to hybridise for half an hour at 37° C. Then the wells were washed five times with 300 µL of 1×SSC with 0.1% Tween 20 (1×SSC is: 150 mM NaCl, 15 mM sodium citrate). Then, 100 µL of 0.12 µM detection probe (EQ-3246, SEQ ID NO 8) dissolved in 1×SSC with 0.1% Tween 20 were added and allowed to hybridise for half an hour at 37° C. Finally the microtiter-plate was washed three times with 1×SSC with 0.1% Tween 20.

The hybrids were detected by binding streptavidin-horseradish peroxidase to the biotinylated detection probe. The strA-HRP (Pierce, Rockford, Ill., U.S.A. Cat. no. 21126) was dissolved in 1×SSC with 0.1% Tween 20 at a concentration of 1 µg/mL. 100 µL was added per well and incubated 15 min. Then the plate was washed three times with 1×SSC; 0.1% Tween 20 and the signal developed in the OPD-assay.

OPD-assay

A master-mix containing: 6 mL of 0.1 M citrate buffer pH=5.0, two 2 mg ortho-phenylene-diamine (OPD) tablets (Kem-En-Tech, Copenhagen, Denmark) and 2.5 µL of 30% H$_2$O$_2$ was prepared. 100 µL of the master-mix is added to each reaction chamber and is left to incubate for one to 30 min. depending on enzyme activity. The assay is stopped with 100 µL of 0.5 M H$_2$SO$_4$ and the optical density is measured at λ=492 nm with an ELISA-reader.

Figures 1, 2:
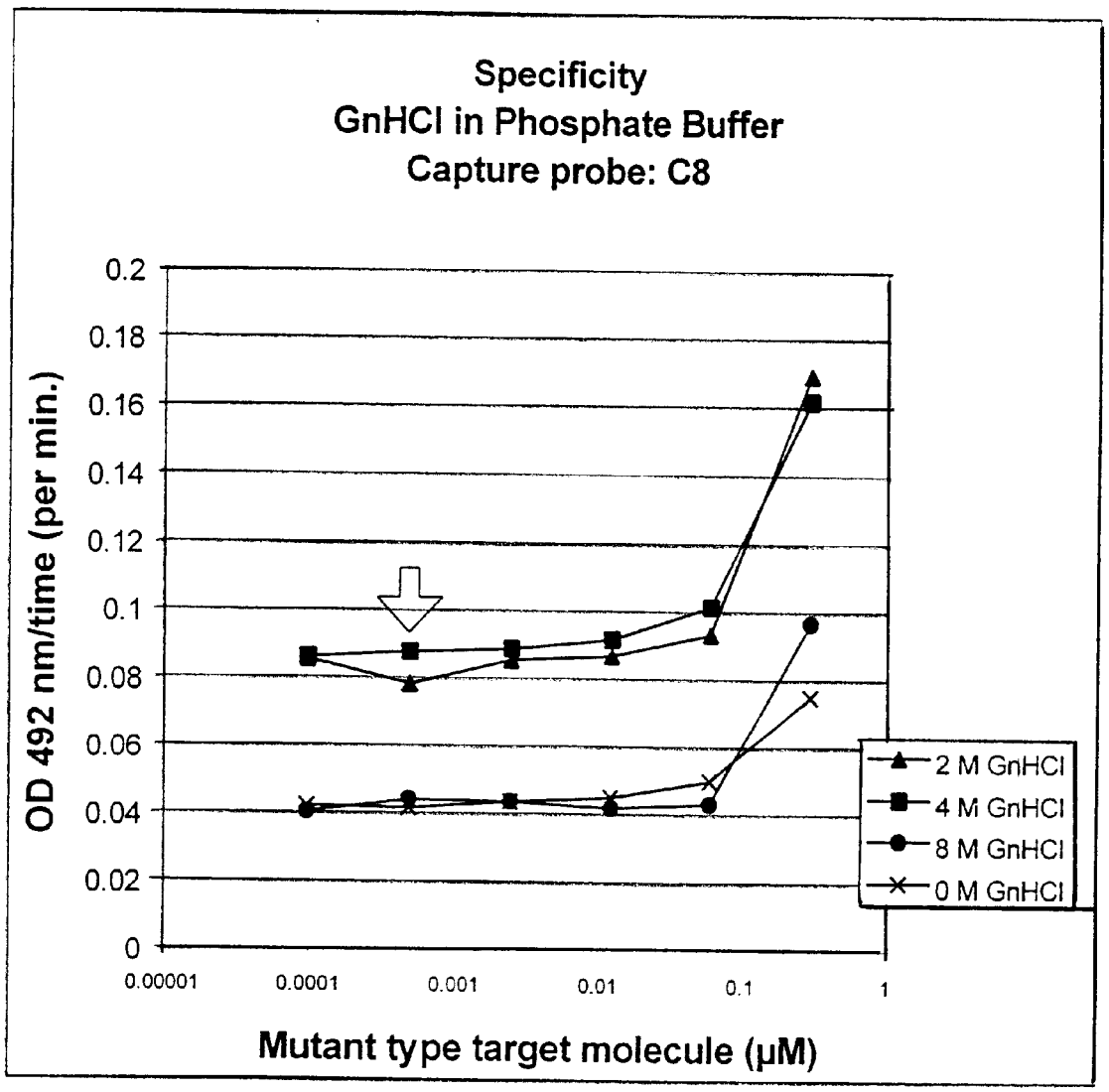
Figure 2:
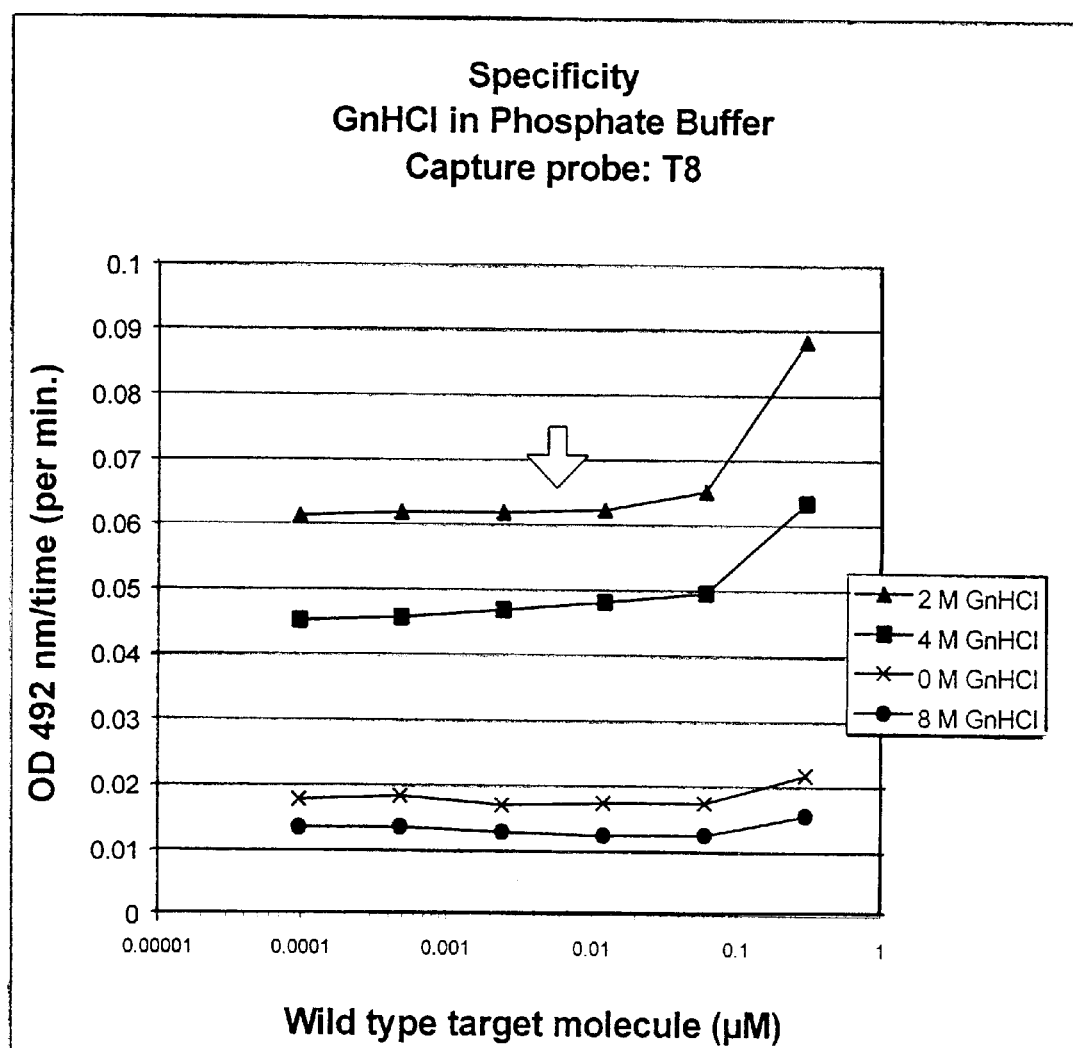

Results:

The results are shown in FIGS. 2-1 and 2-2.

Conclusion

Based on this experiment it is concluded that the stringency of the hybridisation—even at high concentrations of GnHCl—is compatible to the stringency observed in buffer without GnHCl.

With the C8 capture probe a clear increase in (non-specific) signal is not seen until the concentration of competing mutant type target molecule is above 0.05 µM. At this concentration the ratio of matching to mismatching oligo is 1:100. Equal contributions from the matching and the mismatching oligo (e.g. a two-fold increase in signal) is obtained at an amount of 0.2–0.5 µM competing oligo depending on the concentration of GnHCl. High stringency is seen at concentrations up to 4 M GnHCl. In these buffers equal signal is obtained at a ratio of matching to mismatching oligo of approximately 1:600. In other words, a signal to noise ratio of 1:600 is observed.

With the T8 capture probe a clear increase in (non-specific) signal is not seen until the concentration of competing wild type target molecule is above 0.1 µM. At this concentration the ratio of matching to mismatching oligo is 1:20. Equal contributions from the matching and the mismatching oligo (e.g. a two-fold increase in signal) are not obtained at any amount of competing oligo. Thus equal signal is assumed to be obtained at a ratio of matching to mismatching oligo that is higher than 1:60. In other words, a signal to noise ratio is observed that is higher than 1:60 (better than 1:100 extrapolated value).

It is concluded that hybridisation in buffers containing strong chaotrophic agents such as guanidine hydrochloride (GnHCl) can be performed at sufficiently high stringency to allow single-base discrimination.

EXAMPLE 3.

GnSCN Allows and Enhances Hybridization in Sodium Citrate and Phosphate Buffer

Standard lysis buffers for RNA preparation are often based on sodium citrate buffers, e.g.:

Glisin (1974) Biochemistry 13, 2633 and Chirwin (1979) Biochemistry 18, 5294. The following experiment was carried out to compare the hybridisation performance in guanidine thiocyanate (GnSCN) containing buffers based on either sodium citrate or phosphate.

LNA modified oligos (see table 3-1) carrying a 5' anthraquinone were covalently immobilized to the wells of a microtiter-plate by UV irradiation and used as capture probes in a hybridisation assay with a complementary target DNA oligo. The hybrid was detected by including a 5' biotinylated DNA detection probe in the hybridisation mixture.

TABLE 3-1

Oligonucleotides studied

| Name | EQ number | SEQ ID NO | Sequence | Characteristics |
|---|---|---|---|---|
| C8 | EQ-3133 | 4 | 5'-AQ-tac atg tta tgc ttt GAC$^{met}$ C$^{met}$GT GTg-3' | 5' anthraquinone modified LNA |
| T8 | EQ-3134 | 9 | 5'-AQ-tac atg tta tgc ttt GAC$^{met}$ TGT GTg-3' | 5' anthraquinone modified LNA |
| Wild type target molecule | EQ-3185 | 7 | 5'ttg aat tcc aag agc aca cgg tct tca gtg aag ctg cag ggc act tcc aa 3' | Wildtype, sense g/c pos. 9756 (50-mer) |
| Mutation type target molecule | EQ-3187 | 10 | 5'ttg aat tcc aag agc aca cag tct tca gtg aag ctg cag ggc act tcc aa 3' | Sense a/t pos. 9756 (50-mer) |
| Detection probe | EQ-3246 | 8 | 5'-biotin-ttg gaa gtg ccc tgc agc tt-3' | 5' biotinylated DNA |

Note:
LNA monomers are indicated in uppercase letters, DNA monomers are indicated in lowercase letters. C$^{met}$ indicates that the monomer is 5-methyl cytosine LNA. 5'-AQ indicates that the oligo carries a 5'anthraquinone (AQ) and a C3 linker, the composition is AQ—CONH—(CH$_2$)$_3$-oligo. 5'-biotin indicates that the 5'end of the oligo is: Biotin-(CH$_2$)$_4$—CONH—(CH$_2$)$_6$-oligo.

Immobilizing ApoB Capture Probes

Anthraquinone LNA capture probes (either C8 or T8—see table 3-1) were dissolved in 0.2 M NaCl at a concentration of 0.1 μM. 100 μL of the oligos were added to each of the wells of the microtiter plate (C96 polysorp; Nalge Nunc International, Roskilde, Denmark), and exposed for 15 min. to soft UV light (approximately 350 nm) in a ULS-20-2 illuminator (UV-Lights Systems, Denmark) at maximal 35° C. The illuminator is equipped with 28 Philips Cleo Compact 25W-S light bulbs (14 located above and 14 located below the glass plate sample holder); only the upper bulbs were lit.

After incubation the wells were washed with first 300 μL of 0.4 M NaOH with 0.25% Tween 20 (Riedel-de Haen, Seelze, Germany) and then three times with 300 μL of deionized water.

Hybridization With WT (EQ-3185) and MUT (EQ-3187) Target Molecules

Wild type (WT) target molecules (0.012 μM) were added to microtiter-plate wells coated with C8 capture probe. The concentration of GnSCN in the hybridisation mixture was varied in two-fold "dilutions"—see below. The resulting concentrations of GnSCN were: 0.03, 0.06, 0.13, 0.25, 0.5, 1, 2 and 4 M.

Similarly, mutant type (MUT) target molecules (0.012 μM) were added to microtiter-plate wells coated with T8 capture probe and hybridised at 0.03, 0.06, 0.13, 0.25, 0.5, 1, 2 and 4 M GnSCN.

Hybridization buffers were constructed by dissolving solid GnSCN to a final concentration of 4 M either in 40 mM sodium citrate buffer, pH 7, with 0.5% Sarcosyl; or in 50 mM phosphate buffer, pH 7, with 0.1% Tween 20. Buffers with lower concentrations of GnSCN were then constructed by diluting the buffer containing 4 M GnSCN with a similar buffer containing 0 M GnSCN.

100 μL of hybridisation mix were added per microtiter-plate well. The capture and target oligos were allowed to hybridise for half an hour at 37° C. Then the wells were washed five times with 300 μL of 1×SSC with 0.1% Tween 20 (1×SSC is: 150 mM NaCl, 15 mM sodium citrate) Finally, 100 μL of 0.12 μM detection probe (EQ-3246, SEQ ID NO 8) in 1×SSC with 0.1% Tween 20 were added for half an hour at 37° C., and then washed three times with 1×SSC with 0.1% Tween 20.

The hybrids were detected by binding streptavidin-horseradish peroxidase to the biotinylated detection probe. The strA-HRP (Pierce, Rockford, Ill., USA. Cat. no. 21126) was dissolved in 1×SSC with 0.1% Tween 20 at a concentration of 1 μg/mL. 100 μL was added per well and incubated 15 min. Then the plate was washed three times with 1×SSC; 0.1% Tween 20 and the signal developed in the OPD-assay.

OPD-assay

A master-mix containing: 6 mL of 0.1 M citrate buffer pH=5.0, two 2 mg ortho-phenylenediamine (OPD) tablets (Kem-En-Tech, Copenhagen, Denmark) and 2.5 μL of 30% H$_2$O$_2$ was prepared. 100 μL of the master-mix is added to each reaction chamber and is left to incubate for one to 30 min. depending on enzyme activity. The assay is stopped with 100 μL of 0.5 M H$_2$SO$_4$ and the optical density is measured at λ=492 nm with an ELISA-reader.

Results

Figures 1, 3:
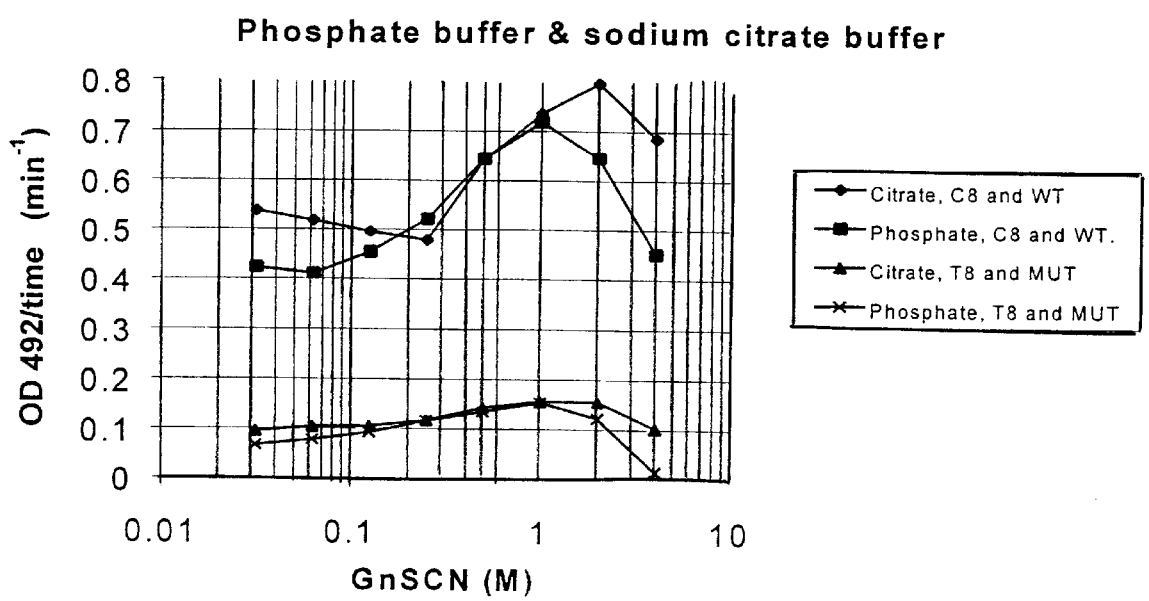
Figures 1, 4:
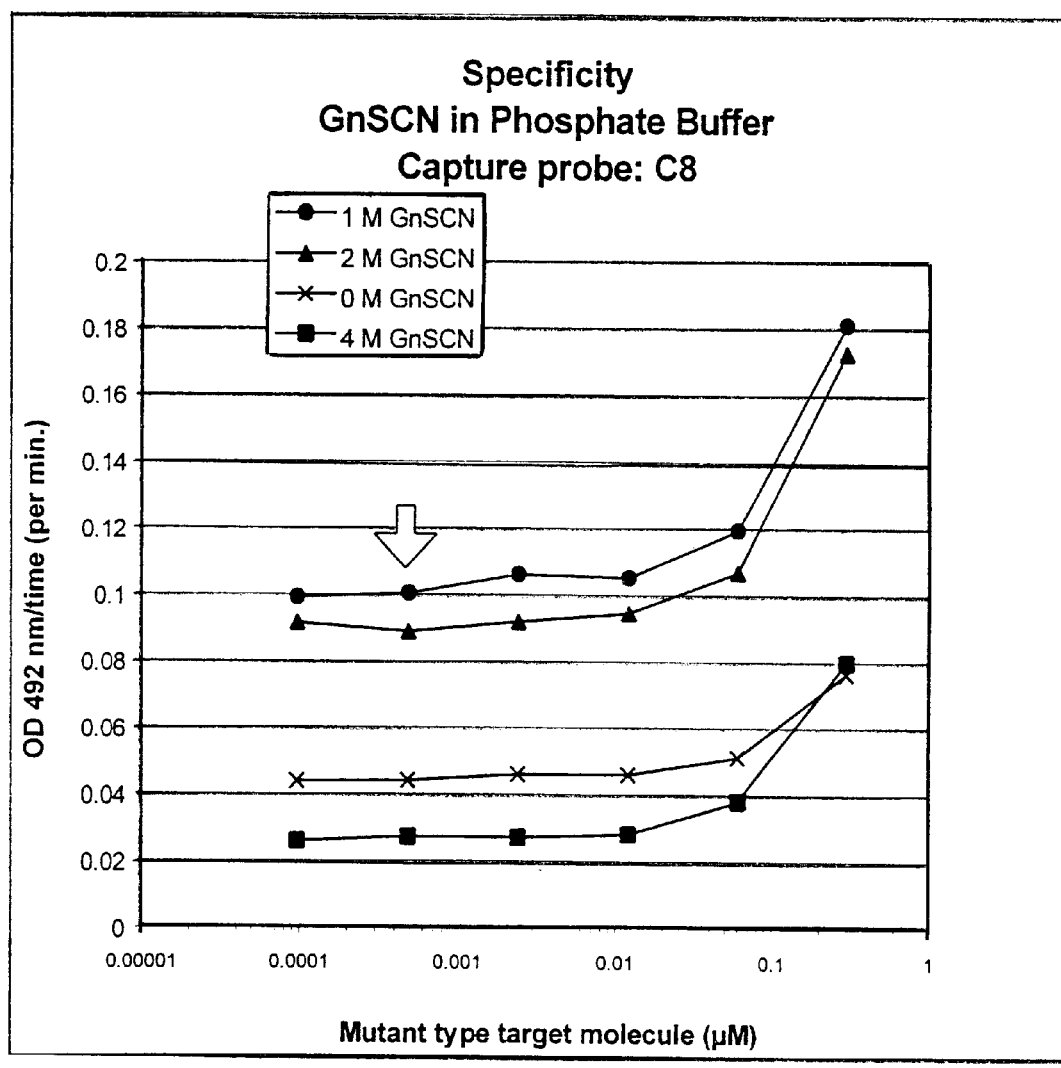
Figures 2, 4:
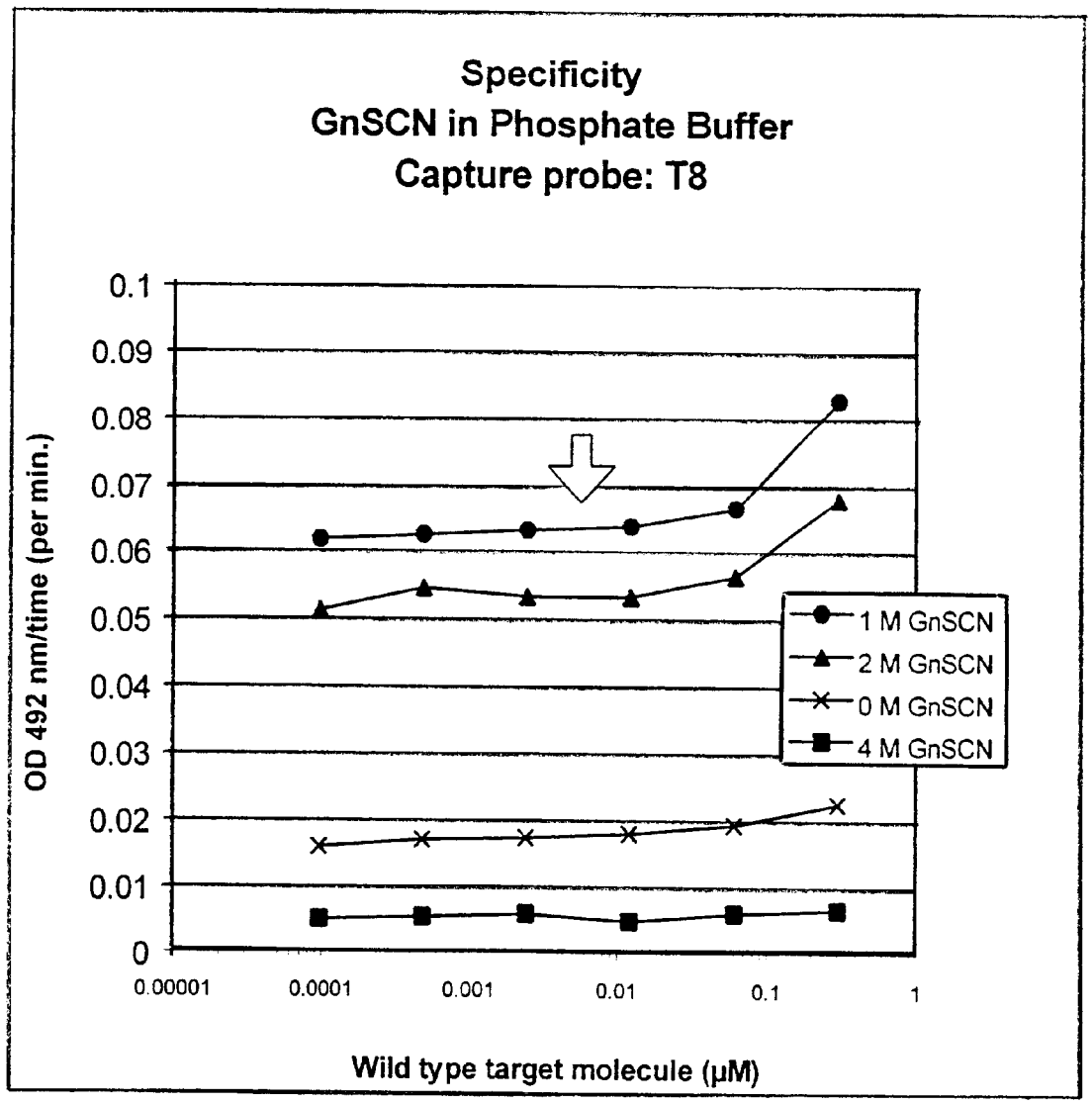
Figures 3, 4:
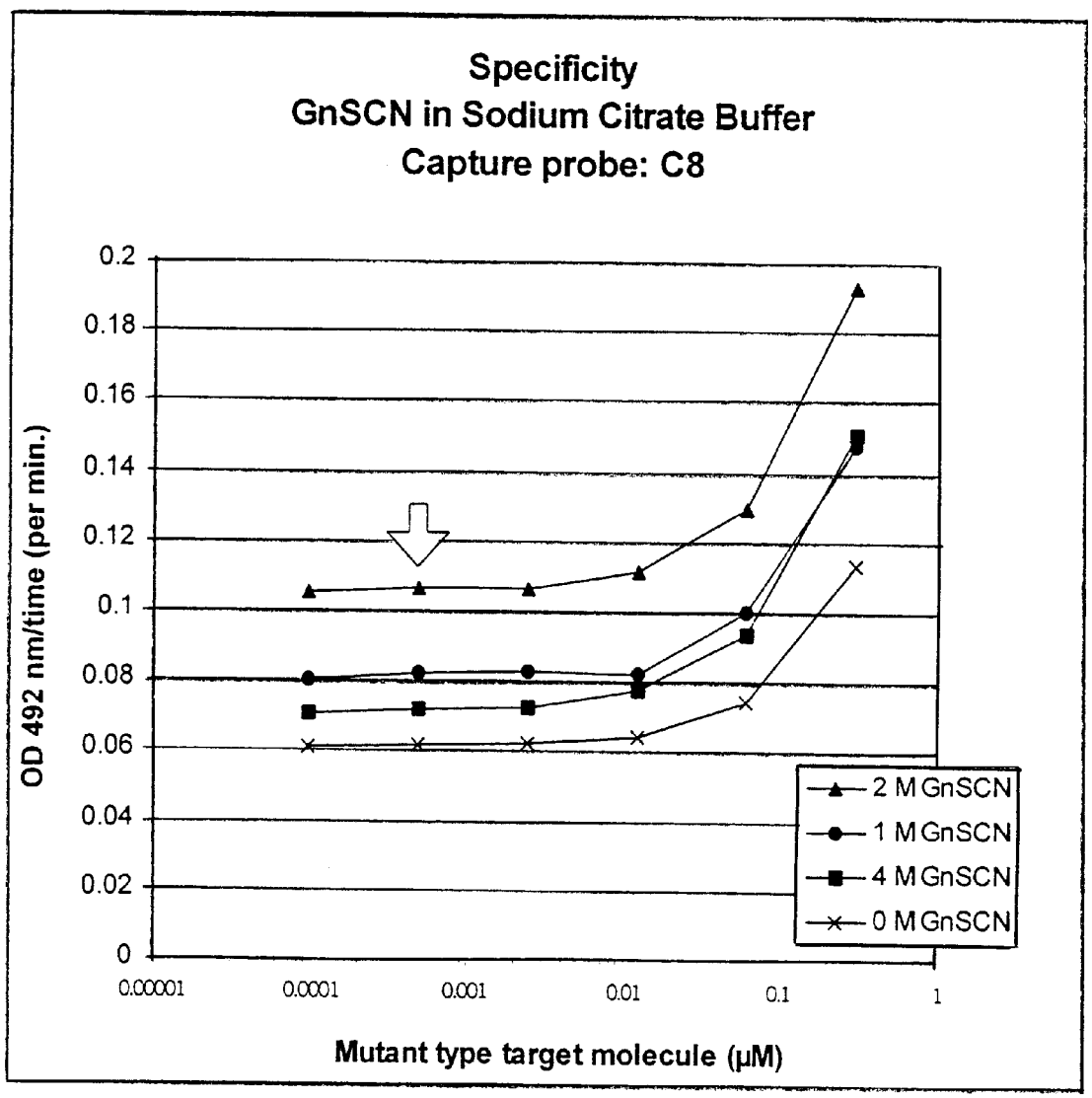
Figure 4:
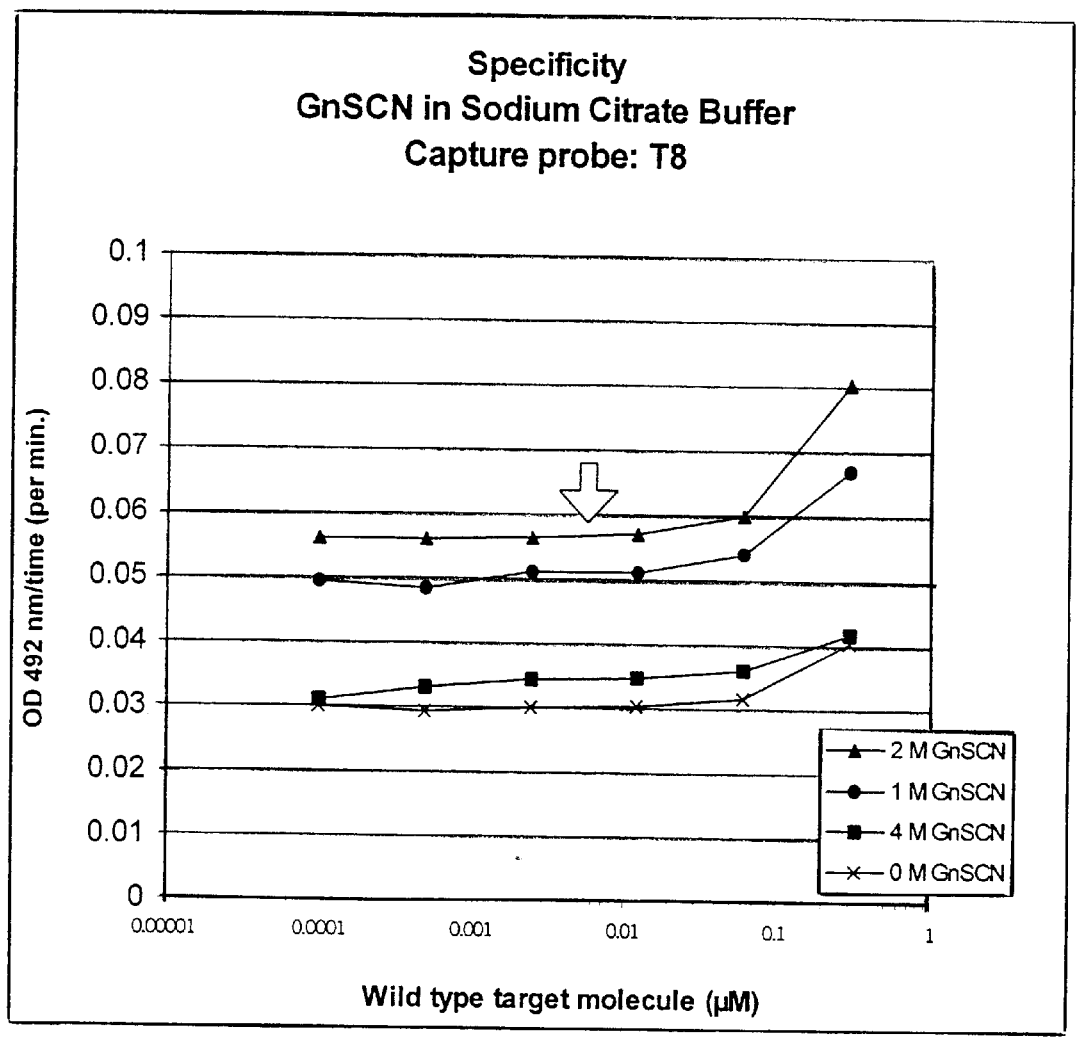

The results are shown in FIG. 3-1.

Conclusion

It is observed that the hybridisation signal is enhanced as a function of GnSCN concentration starting its effect at about 0.2 M and having its optimum from about 1 M to 2 M.

The most prominent enhancement by GnSCN is seen in the hybridisation between the C8 capture LNA probe and the WT target oligo in phosphate based buffers. At optimal concentration of GnSCN the signal was enhanced 75%.

The hybridisation with T8 and MUT oligo is less affected by GnSCN. In phosphate buffer high concentrations of GnSCN (4 M) had a negative effect.

In conclusion it is seen that buffers based on sodium citrate, e.g. the type that is used in many cell lysis-buffers, are at least as good as phosphate-based buffers, and that GnSCN, like guanidine hydrochloride (GnHCl), allows and indeed enhances hybridisation even at high concentrations.

EXAMPLE 4

Hybridization in GnSCN is Specific (Competition Experiment) Comparing Sodium Citrate and Phosphate Buffers The following experiment was carried out to compare the hybridisation stringency in guanidine thiocyanate (GnSCN) containing buffers based on either sodium citrate or phosphate.

LNA modified oligos (see table 2-1) carrying a 5' anthraquinone were covalently immobilized to the wells of a microtiter-plate by UV irradiation and used as capture probes in a hybridisation assay with a complementary target DNA oligo. The hybrid was detected by including a 5' biotinylated DNA detection probe in the hybridisation mixture.

TABLE 4-1

Oligonucleotides studied

| Name | EQ number | SEQ ID NO | Sequence | Characteristics |
|---|---|---|---|---|
| C8 | EQ- | 4 | 5'-AQ-tac atg tta tgc ttt | 5' anthraquinone |

TABLE 4-1-continued

Oligonucleotides studied

| Name | EQ number | SEQ ID NO | Sequence | Characteristics |
|---|---|---|---|---|
| | 3133 | | GAC$^{met}$C$^{met}$GT GTg-3' | modified LNA |
| T8 | EQ-3134 | 9 | 5'-AQ-tac atg tta tgc ttt GAC$^{met}$ TGT GTg-3' | 5' anthraquinone modified LNA |
| Wild type target molecule | EQ-3185 | 7 | 5'ttg aat tcc aag agc aca cgg tct tca gtg aag ctg cag ggc act tcc aa 3' | Wildtype, sense g/c pos. 9756 (50-mer) |
| Mutation type target molecule | EQ-3187 | 10 | 5'ttg aat tcc aag agc aca cag tct tca gtg aag ctg cag ggc act tcc aa 3' | Sense a/t pos. 9756 (50-mer) |
| Detection probe | EQ-3246 | 8 | 5'-biotin-ttg gaa gtg ccc tgc agc tt-3' | 5' biotinylated DNA |

Note:
LNA monomers are indicated in uppercase letters, DNA monomers are indicated in lowercase letters. C$^{met}$ indicates that the monomer is 5-methyl cytosine LNA. 5'-AQ indicates that the oligo carries a 5'anthraquinone (AQ) and a C3 linker, the composition is AQ—CONH—(CH$_2$)$_3$-oligo. 5'-biotin indicates that the 5'end of the oligo is: Biotin-(CH$_2$)$_4$—CONH—(CH$_2$)$_6$-oligo.

Immobilizing ApoB Capture Probes

Anthraquinone LNA capture probes (either C8 or T8—see table 4-1) were dissolved in 0.2 M NaCl at a concentration of 0.1 μM. 100 μL of the oligos were added to each of the wells of the microtiter-plate (C96 polysorp; Nalge Nunc International, Roskilde, Denmark), and exposed for 15 min. to soft UV light (approximately 350 nm) in a ULS-20-2 illuminator (UV-Lights Systems, Denmark) at maximal 35° C. The illuminator is equipped with 28 Philips Cleo Compact 25W-S light bulbs (14 located above and 14 located below the glass plate sample holder); only the upper bulbs were lit.

After incubation the wells were washed with first 300 μL of 0.4 M NaOH with 0.25% Tween 20 (Riedel-de Haen, Seelze, Germany) and then three times with 300 μL of deionized water.

Hybridization With Wild Type Target Molecule (EQ-3185) and Mutation Type Target Molecule (EQ-3187)

To wells coated with C8 capture probe (EQ 3133, SEQ ID NO 4) wild type target molecule (EQ3185, SEQ ID NO 7) was added in a constant low concentration (0.0005 μM) while the amount of the competing single base mismatching mutation type target molecule (EQ3187, SEQ ID NO 10) was varied in a five-fold "dilution series". The resulting concentrations of the mutation type target molecule were: 0.0001, 0.0005, 0.0025, 0.012, 0.06 and 0.30 μM.

To chambers coated with T8 capture probe (EQ3134, SEQ ID NO 9) mutation type target molecule was added in a constant low concentration (0.005 μM) while the amount of the competing single base mismatching wild type target molecule (EQ3185, SEQ ID NO 7) was varied in a five-fold "dilution series". The resulting concentrations of the wild type target molecule were: 0.0001, 0.0005, 0.0025, 0.012, 0.06 and 0.30 μM.

Hybridization buffers were constructed by dissolving solid GnSCN to a final concentration of 4 M either in 40 mM sodium citrate buffer, pH 7, with 0.5% Sarcosyl; or in 50 μM phosphate buffer, pH 7, with 0.1% Tween 20. Buffers with lower concentrations of GnSCN were then constructed by diluting the buffer containing 4 M GnSCN with a similar buffer containing 0 M GnSCN.

100 μL of hybridisation mix were added per microtiter-plate well. The capture and target oligos were allowed to hybridise for half an hour at 37° C. Then the wells were washed five times with 300 μL of 1×SSC with 0.1% Tween 20 (1×SSC is: 150 mM NaCl, 15 mM sodium citrate). Then, 100 μL of 0.12 μM detection probe (EQ-3246, SEQ ID NO 8) dissolved in 1×SSC with 0.1% Tween 20 were added and allowed to hybridise for half an hour at 37° C. Finally the microtiter-plate was washed three times with 1×SSC with 0.1% Tween 20.

The hybrids were detected by binding streptavidin-horseradish peroxidase to the biotinylated detection probe. The strA-HRP (Pierce, Rockford, Ill., USA. Cat. no. 21126) was dissolved in 1×SSC with 0.1% Tween 20 at a concentration of 1 μg/mL. 100 μL was added per well and incubated 15 min. Then the plate was washed three times with 1×SSC; 0.1% Tween 20 and the signal developed in the OPD-assay.

OPD-assay

A master-mix containing: 6 mL of 0.1 M citrate buffer pH=5.0, two 2 mg ortho-phenylenediamine (OPD) tablets (Kem-En-Tech, Copenhagen, Denmark) and 2.5 μL of 30% H$_2$O$_2$ was prepared. 100 μL of the master-mix is added to each reaction chamber and is left to incubate for one to 30 min. depending on enzyme activity. The assay is stopped with 100 μL of 0.5 M H$_2$SO$_4$ and the optical density is measured at λ=492 nm with an ELISA-reader.

Results

The results are shown in FIGS. 4-1, 4-2, 4-3 and 4-4.

Conclusion

Based on this experiment it is concluded that the stringency of the hybridisation—even at high concentrations of GnSCN—is compatible to the stringency observed in buffer without GnSCN. It is furthermore concluded that the stringency is comparable in sodium citrate- and phosphate-based buffers.

With the C8 capture probe a clear increase in (non-specific) signal is not seen until the concentration of competing mutant type target molecule is above 0.05 μM. At this concentration the ratio of matching to mismatching oligo is 1:100. Equal contributions from the matching and the mismatching oligo (e.g. a two-fold increase in signal) is, with the exception of C8 hybridisation in 4 M GnSCN, PO$_4$-buffer, not obtained at any amount of competing oligo. In the case of the hybridisation to C8 in 4 M GnSCN, PO$_4$ equal signal is obtained at approximately 0.15 μM indicating a signal to noise ratio of approximately 300. In the remaining hybridisations the signal to noise ratio is better than 1:600.

With the T8 capture probe a clear increase in (non-specific) signal is not seen until the concentration of competing wild type target molecule is over 0.1 μM. At this concentration the ratio of matching to mismatching oligo is 1:20. Equal contributions from the matching and the mismatching oligo (e.g. a two-fold increase in signal) is not obtained at any amount of competing oligo. Thus equal signal is assumed to be obtained at a ratio of matching to mismatching oligo that is higher than 1:60. In other words, a signal to noise ratio that is higher than 1:60 is observed.

The hybridisation stringency is almost the same in buffers based on either sodium citrate or phosphate. However, higher hybridisation signals were obtained in sodium citrate based buffers.

It is concluded that hybridisation in buffers containing strong chaotrophic agents such as in guanidine thiocyanate (GnSCN) can be performed at sufficiently high stringency to allow detection of single base differences and that buffers based on either sodium citrate or phosphate can be used.

EXAMPLE 5

Thermostability of DNA and LNA Oligonucleotides in Buffers Containing Guanidine Hydrochloride The thermostability of the all-DNA and LNA modified oligonucleotides was determined spectrophotometrically using a spectrophotometer equipped with a thermoregulated Peltier element (Perkin Elmer, UV Lambda 40). Hybridization mixtures of 1 ml were prepared containing either of 2 different buffers (4 M GnHCl in 50 mM Na—PO$_4$, pH 6.8, 0.1 mM EDTA; or 50 mM Na—PO$_4$, pH 6.8, 115 mM NaCl, 0.1 mM EDTA) and equimolar (1 μM) amounts of the LNA modified oligonucleotides and their complementary or mismatched DNA oligonucleotides. Identical hybridisation mixtures using the unmodified oligonucleotides were prepared as references.

Each sample was heated in an eppendorf tube to 90° C. in a heating block and allowed to cool slowly within the turned off heating block to room temperature. The sample was transferred into a 500 μL quartz cuvette (Perkin Elmer). Samples were then measured on the UV Lambda 40 spectrophotometer. The samples were measured at 260 nm while the temperature was raised with 1° C. per minute. The $T_m$'s were obtained as the first derivative of the melting curves. Table 5-2 summarizes the results. Table 5-1 summarizes the oligos used.

TABLE 5-1

Oligonucleotides studied

| Name | EQ number | SEQ ID NO | Sequence | Characteristics |
|---|---|---|---|---|
| 112T | EQ-3485 | 11 | 5'-C$^{met}$GC$^{met}$ AC$^{met}$A C$^{met}$Gt-3' | LNA |
| as112t | EQ-3493 | 12 | 5'-acg tgt gcg-3' | LNA |
| as112c | EQ-3495 | 13 | 5'-acg tgc gcg-3' | all-DNA |
| 158T | EQ-3489 | 14 | 5'-GGC$^{met}$ AC$^{met}$T TC$^{met}$t-3' | LNA |
| as158t | EQ-3497 | 15 | 5'-aga agt gcc-3' | LNA |
| as158c | EQ-3499 | 16 | 5'-aga agc gcc-3' | all-DNA |

Note:
LNA monomers are indicated in uppercase letters, DNA monomers are indicated in lowercase letters. C$^{met}$ indicates that the monomer is 5-methyl cytosine LNA.

Results

Table 5-2 shows the thermostability of DNA and LNA oligonucleotides in buffers containing guanidine hydrochloride.

TABLE 5-2

| oligo pair | match | $T_m$ in hybridisation buffer containing | |
|---|---|---|---|
| | | 165 mM Na$^+$ | 4 M GnHCl |
| LNA (EQ3485):DNA (EQ3493) | perfect match | 73.8° C. | 65.4° C. |
| LNA (EQ3485):DNA (EQ3495) | one mismatch | 51.5° C. (ΔT$_m$ 22.3° C.) | 41.1° C. (ΔT$_m$ 24.3° C.) |
| LNA (EQ3489):DNA (EQ3497) | perfect match | 69.9° C. | 61.2° C. |
| LNA (EQ3489):DNA (EQ3499) | one mismatch | 47.0° C. (ΔT$_m$ 22.9° C.) | 33.2° C. (ΔT$_m$ 28.0° C.) |

Note:
ΔT$_m$ indicates the difference in T$_m$ between the perfect matching LNA:DNA hetero-duplex and the duplex in question.

Conclusion

From the experiment it is concluded that hybridisation occurs in buffers containing high concentrations of strong chaotrophic agents.

When a single mismatch is introduced into the target DNA oligonucleotides, the T$_m$ of LNA:DNA heteroduplexes drops significantly. The results indicate that the T$_m$ change is more pronounced in guanidine containing buffers compared to standard buffers, suggesting that hybridisation buffers containing strong chaotrophic agents may be advantageous for single base discrimination by hybridisation.

EXAMPLE 6

Detection of Single Base Polymorphism by Hybridisation of PCR Products to LNA Capture Oligos As a first step to test if it is possible to detect a specific sequence in a complex biological sample, the following experiment was carried out.

The product of the PCR is considerably more complex than adding synthetic 50'mer template, and this may challenge the hybridisation process. To test if hybridisation in chaotrophic buffers was sufficiently discriminatory and sensitive, PCR reactions were performed on various templates containing either wild type or mutant type ApoB3500, and tested in a LNA hybridisation assay. The assay consisted of 5' anthraquinone immobilized LNA modified oligos (see table 6-1) functioning as capture probe and the PCR product as complementary target DNA oligo. The hybrid was detected by binding streptavidin-horseradish peroxidase to the biotinylated end of the PCR product and afterwards performing an OPD assay.

TABLE 6-1

Oligonucleotides applied

| Name | EQ number | SEQ ID NO | Sequence | Characteristics |
|---|---|---|---|---|
| C8 | EQ-3133 | 4 | 5'-AQ-tac atg tta tgc ttt GAC$^{met}$ C$^{met}$GT GTg-3' | 5' anthraquinone modified LNA |
| T8 | EQ-3134 | 9 | 5'-AQ-tac atg tta tgc ttt GAC$^{met}$ TGT GTg-3' | 5' anthraquinone modified LNA |
| Forward primer | EQ-3198 | 17 | 5'-biotin-cta gtg agg cca aca ctt act tga att cca aga gc-3' | 5' biotinylated DNA primer, sense (35-mer) |
| Backward primer | EQ-3213 | 3 | 5'-gtt ttt cgt act gtg ctc cca gag-3' | DNA primer, sense (24-mer) |

Note:
LNA monomers are indicated in uppercase letters, DNA monomers are indicated in lowercase letters. C$^{met}$ indicates that the monomer is 5-methyl cytosine LNA. 5'-AQ indicates that the oligo carries a 5' anthraquinone (AQ) and a C3 linker, the composition is AQ—CONH—(CH$_2$)$_3$-oligo. 5'-biotin indicates that the 5'end of the oligo is: Biotin-(CH$_2$)$_4$—CONH—(CH$_2$)$_6$-oligo.

TABLE 6-2

PCR template

| Sample | Source | Characteristics |
|---|---|---|
| HCV29 | Human DNA | ApoB35000, wild type, sense g/c pos. 9756 |
| T112C1 | Human DNA | ApoB35000, wild type, sense g/c pos. 9756 |
| T112D1 | Human DNA | ApoB35000, wild type, sense g/c pos. 9756 |
| "A-allele"-plasmid | Plasmid | ApoB35000, mutant type, sense a/t pos. 9756 |

Note:
With the forward and backward primers applied on these total DNA or plasmid preparations the expected PCR amplified fragment is 167 bp long and will be 5' biotinylated on the sense strand.

Synthesis and Analysis of Primers

DNA primers were obtained as HPLC purified oligos from a commercial source (DNA Technology, Aarhus, Denmark).

Sample Preparation

1) Human genomic DNA:

Human genomic DNA was isolated by standard phenol extraction (Sambrook et al. (1989) Molecular Cloning, 2nd ed. Cold Spring Harbor Laboratory Press, Cold Spring Harbor, N.Y.) from 3 different human cancer cell lines: HCV29, T 112C1, T 112D1 (Skouv et al. (1989) Mol Carcin. 2, 59–62) that are wildtype with respect to the ApoB3500 polymorphism (Ludwig et al. (1987) DNA 6: 363–372; accession no. M 19828).

2) "A-allele"-plasmid:

Human genomic DNA was isolated from 5 ml of whole blood, using the DNA Isolation Kit for Mammalian Blood (Roche Molecular Systems cat. no. 1 667 327. Roche Molecular Biochemicals, Hvidovre, Denmark) and closely following the recommendations of the manufacturer.

The "A-allele" of the ApoB gene was generated by PCR-amplification of part of the wild type human ApoB gene comprising the ApoB3500 locus. The PCR fragment was cloned into plasmid pCR®2.1-TOPO using the TOPO™ TA Cloning® Kit (Invitrogen, cat. no. K4500-01, Invitrogen Corporation, Carlsbad Calif. USA). Plasmid DNA was purified from bacterial cultures, using QUIAGEN® Plasmid Kits (QIAGEN GmbH, Hilden, Germany). The DNA sequence of the insert was verified by DNA sequencing using an ALFexpress II DNA Analysis System (Amersham Pharmacia Biotech) and closely following the recommendations of the manufacturer.

PCR on Sample Preparations

PCR master-mix for 6 reactions:

148.50 µL $H_2O$

30 µL 10×AmpliTaq Gold buffer (Perkin-Elmer Corporation, Norwalk, Conn., USA).

18 µL $MgCl_2$ (25 mM)

30 µL dNTP (2 mM)

30 µL forward primer EQ3198 (SEQ ID NO 17) (10 µM)

30 µL backward primer EQ3213 (SEQ ID NO 3) (10 µM)

1.5 µL AmpliTaq Gold® DNA Polymerase (5 U/µL) (Perkin Elmer cat. no. N808-0240, Perkin-Elmer Corporation, Norwalk, Conn., USA).

PCR Amplification

The PCR reactions were carried out in 0.5 mL thin-wall tubes using an Eppendorf Mastercycler Gradient thermocycler (Eppendorf—Netheler—Hinz GmbH, Hamburg, Germany). To 48 µL master-mix 2 µL sample were added.

Termocycling

Denaturation: 94° C., 15 min.

Amplification (30 cycles): 94° C., 40 sec.; 56° C., 40 sec.; 72° C., 40 sec.

Elongation: 72° C., 10 min.

Termination: 4° C., ∞.

Detection

The PCR products were subsequently analyzed by standard gel electrophoresis on a 2% agarose gel (LE, Analytical Grade; Promega Corporation, Madison, USA) including Gel-Star® (FMC BioProducts, Rockland, Me., USA) diluted 1:30.000 in the gel and 1×Tris-acetate/EDTA electrophoresis buffer (0.04 M Tris-acetate; 0.001 M EDTA). To 5 µL of each PCR reaction 1 µL of 6×loading buffer (40% sucrose, 0.25% bromophenol blue, 0.25% xylene cyanol, 0.1 M EDTA pH 8.0) was added). The gel was run for approximately 1 h at a constant voltage of 7 V/cm.

For permanent record the gel was photographed by standard Polaroid (Polaroid LTD., St. Albans, UK) photography using an appropriate UV-transilluminator (Model TM-20E UV Products, Upland, Calif., USA) and filter (Kodak Wratten #9 Eastman Kodak Co., Rochester, N.Y., USA).

Immobilizing ApoB Capture Probes

Anthraquinone LNA capture probes (either C8 or T8—see table 6-1) were dissolved in 0.2 M NaCl at a concentration of 0.1 µM. 100 µL of the oligos were added to each of the wells of the microtiter-plate (C96 polysorp; Nalge Nunc International, Roskilde, Denmark), and exposed for 15 min. to soft UV light (approximately 350 nm) in a ULS-20-2 illuminator (UV-Lights Systems, Denmark) at a maximal temperature of 35° C. The illuminator is equipped with 28 Philips Cleo Compact 25W-S light bulbs (14 located above and 14 located below the glass plate sample holder); only the upper bulbs were lit.

After incubation the wells were washed with first 300 µL of 0.4 M NaOH with 0.25% Tween 20 (Riedel-de Häen, Seelze, Germany) and then three times with 300 µL of deionized water.

Hybridisation With PCR Reaction

To chambers with immobilized C8 or T8 capture probe 5 µL of PCR reaction together with 95 µL of 2 M GnSCN sodium citrate buffer were added and left to incubate for half an hour at 37° C.

Hybridisation buffers were 2 M GnSCN in 40 mM sodium citrate buffer, pH 7, with 0.5% Sarcosyl.

After hybridisation the wells were washed five times with 300 µL of 1×SSC with 0.1% Tween 20 (1×SSC is: 150 mM NaCl, 15 mM sodium citrate).

The hybrids were detected by binding streptavidin-horseradish peroxidase to the biotinylated PCR product. The strA-HRP (Pierce, Rockford, Ill., USA. Cat. no. 21126) was dissolved in 1×SSC with 0.1% Tween 20 at a concentration of 1 µg/mL. 100 µL was added per well and incubated 15 min. Then the plate was washed three times with 1×SSC; 0.1% Tween 20 and the signal developed in the OPD-assay.

OPD-assay

A master-mix containing: 6 mL of 0.1 M citrate buffer pH=5.0, two 2 mg ortho-phenylenediamine (OPD) tablets (Kem-En-Tech, Copenhagen, Denmark) and 2.5 µL of 30% $H_2O_2$ as prepared. 100 µL of the master-mix is added to each reaction chamber and is left to incubate for one to 30 min. depending on enzyme activity. The assay is stopped with 100 µL of 0.5 M $H_2SO_4$ and the optical density is measured at λ=492 nm with an ELISA-reader.

Results

Figures 1, 6:
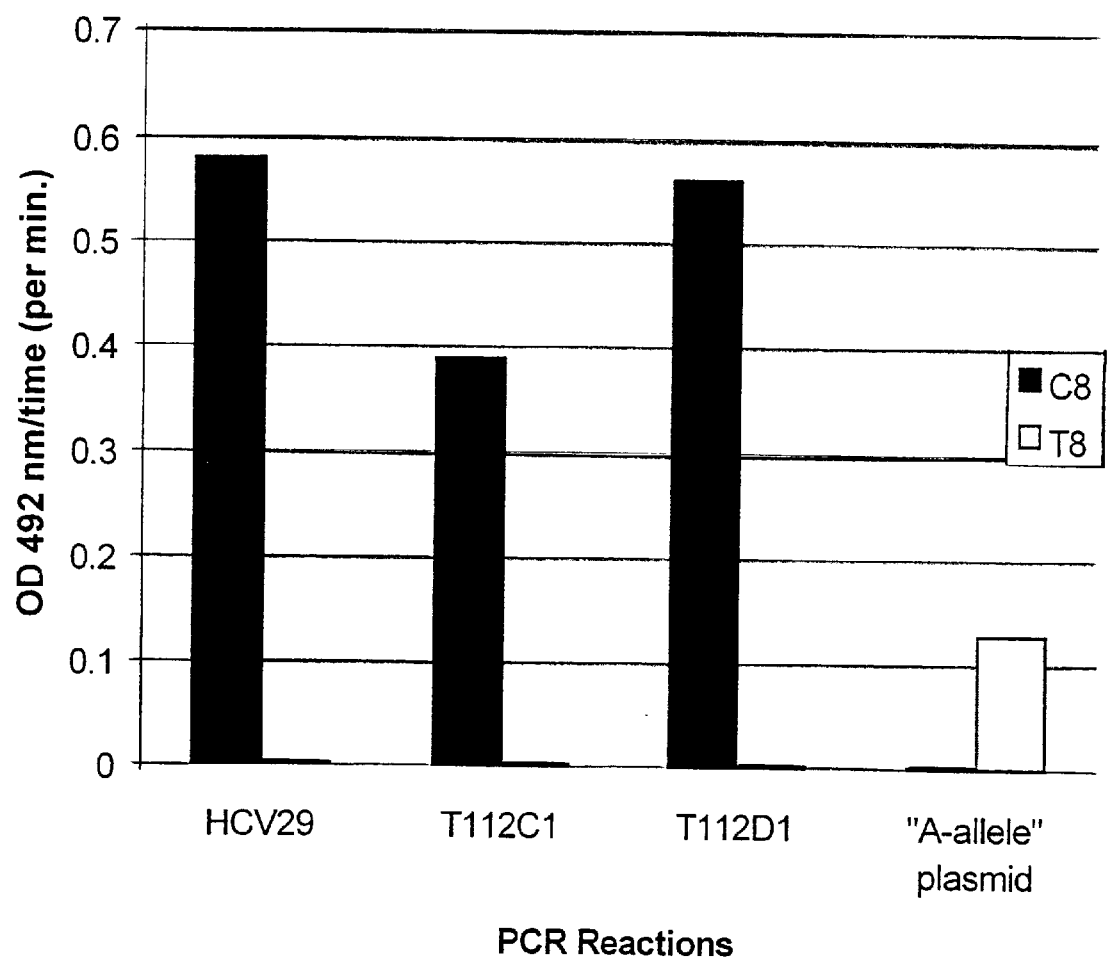

The results are shown in FIG. 6-1.

Conclusion

In all four PCR reactions it is possible to detect single base differences by hybridisation in 2 M GnSCN. As seen also in the previous examples the signal for "A-allele" capture probe (T8) is lower than the signal obtained with the C8 LNA capture probe, yet the signal is very clear also in this case, indicating that hybridisation in 2 M GnSCN is highly stringent.

EXAMPLE 7

Detection of Plasmid DNA in Bacterial Cell Lysate

To study if the hybridisation and extraction methods of the present invention may be applied to a complex biological mixture of nucleic acid and non-nucleic acid, the following experiment was carried out.

Briefly, three different strains of bacteria (*E. coli* K12), two plasmid-containing and one strain without plasmid (see table 7-1), were cultured, lysed, and the plasmid was detected by hybridisation in a guanidine thiocyanate (GnSCN) containing buffer.

TABLE 7-1

Bacterial Strains.

| strain name | genotype | reference |
|---|---|---|
| NF1815 | MC1000 recA1 | Casadaban (1980) J. Mol. Biol. 138, 179–207. |
| TOP10/ pCR | F⁻mcrA_(mrr-hsdRMS-mcrBC) _80lacZ_M15_lac_74 recA1 deoR araD139_(ara-leu) 7697 galU galK rpsL (Str$^R$) endA1 nupG/pCR ®2.1-TOPO | Invitrogen, cat. no. K4500-01, Invitrogen Corporation, Carlsbad CA USA |
| TOP10/ pApoBwt | F⁻mcrA_(mrr-hsdRMS-mcrBC) _80lacZ_M15_lac_74 recA1 deoR araD139_(ara-leu) 7697 galU galK rpsL (Str$^R$) endA1 nupG/pApoBwt | |

Cloning of ApoBwt Plasmid

Human genomic DNA was isolated from 5 ml of whole blood, using the DNA Isolation Kit for Mammalian Blood (Roche Molecular Systems cat. no. 1 667 327. Roche Molecular Biochemicals, Hvidovre, Denmark) and closely following the recommendations of the manufacturer.

The "G-allele" of the ApoB gene was generated by PCR-amplification of part of the wild type human ApoB gene comprising the ApoB3500 locus (Ludwig et al. (1987) DNA 6: 363–372; accession no. M19828, SEQ ID NO 1 and SEQ ID NO 2). The PCR fragment was cloned into plasmid pCR®2.1-TOPO using the TOPO™ TA Cloning® Kit (Invitrogen, cat. no. K4500-01, Invitrogen Corporation, Carlsbad Calif. USA). Plasmid DNA was purified from bacterial cultures, using QUIAGEN® Plasmid Kits (QIAGEN GmbH, Hilden, Germany). The DNA sequence of the insert was verified by DNA sequencing using an ALFexpress II DNA Analysis System (Amersham Pharmacia Biotech) and closely following the recommendations of the manufacturer. The resulting plasmid was named pApoBwt.

The TOP10/pCR strain contains the pCR®2.1-TOPO plasmid without any ApoB insert.

Preparation of Bacterial Cell Lysate

Bacteria were grown in LB media (Sambrook et al. (1989) Molecular Cloning, 2nd ed. Cold Spring Harbor Laboratory Press, Cold Spring Harbor, N.Y.) with 100 µg/mL ampicillin overnight at 37° C. on a shaking device.

The next day the cells were centrifuged (15 min, 8000 r/min) and then resuspended in 1/50 volume 50 mM Tris-Cl (pH 8). The cells were then either sonicated for 45 sec. on ice or added 0.250 mL 100 mg/mL lysozyme for every 2.5 mL resuspended celles and left to incubate for 15 min. at room temperature. The lysed cells were then kept at –20° C.

Detection

LNA modified oligos (see table 7-2) carrying a 5' anthraquinone were covalently immobilized to the wells of a microtiter-plate by UV irradiation and used as capture probes in a hybridisation assay with a complementary target DNA oligo. The hybrid was detected by including a 5' biotinylated DNA detection probe in the post-hybridisation mixture.

TABLE 7-2

Oligonucleotides studied

| Name | EQ number | SEQ ID NO | Sequence | Characteristics |
|---|---|---|---|---|
| C11 | EQ-3131 | 5 | 5'-AQ-tac atg tta tgc ttt AAG AC$^{met}$C$^{met}$GTG TGc-3' | 5' anthraquinone modified LNA |
| T11 | EQ-3132 | 18 | 5'-AQ-tac atg tta tgc ttt AAG AC$^{met}$T GTG TGc-3' | 5' anthraquinone modified LNA |
| Detection probe | EQ-3246 | 8 | 5'-biotin-ttg gaa gtg ccc tgc agc tt-3' | 5' biotinylated DNA |

Note:
LNA monomers are indicated in uppercase letters, DNA monomers are indicated in lowercase letters. C$^{met}$ indicates that the monomer is 5-methyl cytosine LNA. 5'-AQ indicates that the oligo carries a 5'anthraquinone (AQ) and a C3 linker, the composition is AQ—CONH—(CH$_2$)$_3$-oligo. 5'-biotin indicates that the 5'end of the oligo is: Biotin-(CH$_2$)$_4$—CONH—(CH$_2$)$_6$-oligo.

Immobilizing ApoB Capture Probes

Anthraquinone LNA capture probes (C11, T11—see table 7-1) were dissolved in 0.2 M NaCl at a concentration of 0.1 µM. 100 µL of the oligos were added to each of the wells of the microtiter plate (C96 polysorp; Nalge Nunc International, Roskilde, Denmark), and exposed for 15 min. to soft UV light (approximately 350 nm) in a ULS-20-2 illuminator (UV-Lights Systems, Denmark) at maximal 35° C. The illuminator is equipped with 28 Philips Cleo Compact 25W-S light bulbs (14 located above and 14 located below the glass plate sample holder); only the upper bulbs were lit.

After incubation the wells were washed with first 300 µL of 0.4 M NaOH with 0.25% Tween 20 (Riedel-de Häen, Seelze, Germany) and then three times with 300 µL of deionized water.

Hybridization

50 µL of the bacterial cell lysate was mixed with 50 µL (4 M GnSCN, 25 mM sodium citrate, pH 7, 0.5% Sarcosyl) and added to microtiter-plate wells coated with either C8 or T8 LNA capture probe. The mixture was allowed to incubate overnight at 37° C.

Then the wells were washed five times with 300 µL of 1×SSC with 0.1% Tween 20 (1×SSC is: 150 mM NaCl, 15 mM sodium citrate). 100 µL of 0.12 µM detection probe (EQ-3246, SEQ ID NO 8) in 1×SSC with 0.1% Tween 20 were added and allowed to hybridise overnight at 37° C., and then washed three times with 1×SSC with 0.1% Tween 20.

The hybrids were detected by binding streptavidin-horseradish peroxidase to the biotinylated detection probe. The strA-HRP (Pierce, Rockford, Ill., USA. Cat. no. 21126) was dissolved in 1×SSC with 0.1% Tween 20 at a concentration of 1 µg/mL. 100 µL was added per well and incubated 15 min. Then the plate was washed three times with 1×SC; 0.1% Tween 20 and the signal developed in the OPD-assay.

OPD-assay

A master-mix containing: 6 mL of 0.1 M citrate buffer pH=5.0, two 2 mg ortho-phenylenediamine (OPD) tablets (Kem-En-Tech, Copenhagen, Denmark) and 2.5 µL 30% H$_2$O$_2$ was prepared. 100 µL of the master-mix is added to each reaction chamber and is left to incubate for one to 30 min. depending on enzyme activity. The assay is stopped with 100 µL of 0.5 M H$_2$SO$_4$ and the optical density is measured at λ=492 nm with an ELISA-reader.

Results

Figures 1, 7:
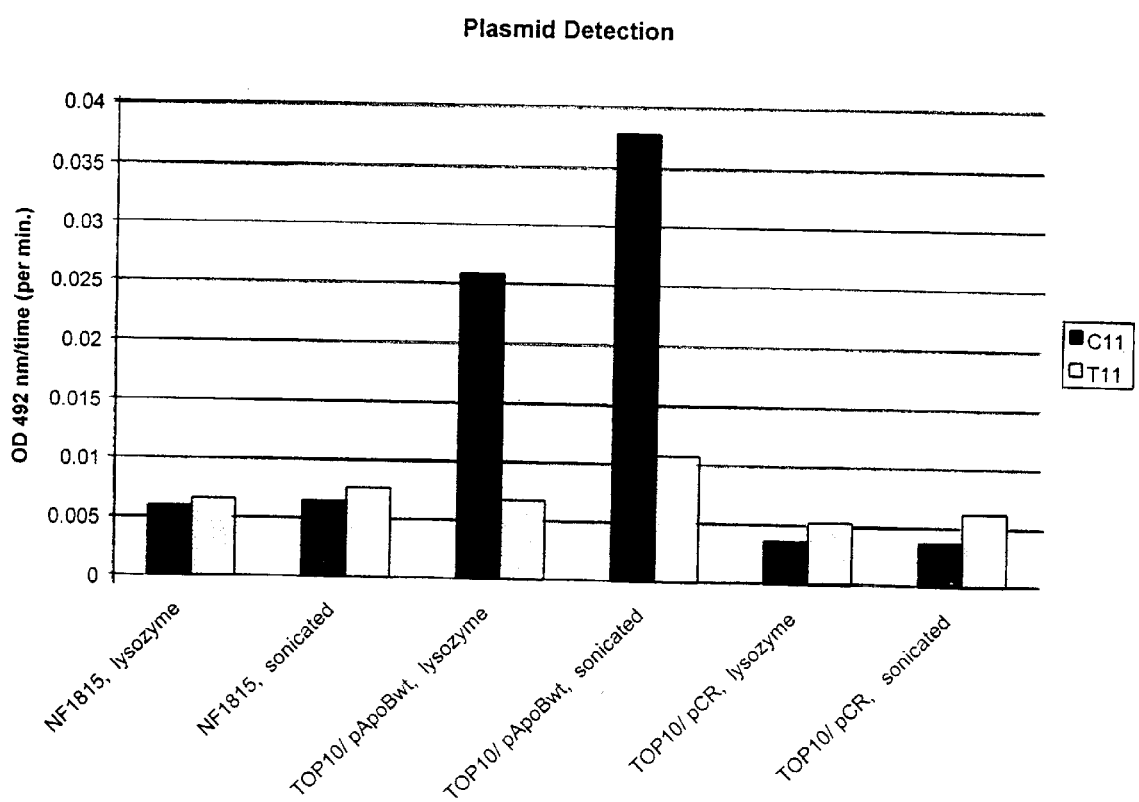

The results are shown in FIG. 7-1.

Conclusion

From the results it is concluded that the pApoBwt plasmid can be captured and detected both in bacteria lysed by sonication and lysozyme treatment. Since plasmids are double-stranded, supercoiled DNA molecules, this experiment indicates that it is possible to detect double-stranded, supercoiled DNA molecules in a complex biological sample such as a crude bacterial lysate.

What is claimed is:

1. A method for isolating a target nucleic acid comprising
   a) providing a sample containing nucleic acids,
   b) treating the sample with a lysing buffer containing a chaotropic agent to lyse cellular material in the sample, dissolve the components and denature the nucleic acids in the sample,
   c) contacting the nucleic acids released from the sample with at least one capturing LNA-probe, said capturing probe being substantially complementary to the target nucleic acid.

2. A method according to claim 1, wherein the capturing LNA-probe is covalently attached to a ligand.

3. A method according to claim 1, wherein the capturing LNA-probe is covalently attached to a solid surface.

4. A method according to claim 2, wherein the ligand covalently attached to the LNA-probe is coupled to an anti-ligand, said anti-ligand being covalently attached to a solid surface.

5. A method according to claims 3 or 4, wherein after the contact of the nucleic acids released from the sample with the LNA attached to the solid surface, the solid surface is separated from excess material.

6. A method according to claim 5, wherein the solid surface is washed with buffer to remove excess material.

7. A method according to claim 1 wherein the capturing probe is complementary to the target nucleic acid.

8. A method according to claim 1 wherein the capturing probe is between 4 and 50 nucleotides long.

9. A method according to claim 1 wherein the capturing probe is between 8 and 30 nucleotides long.

10. A method according to claim 1 wherein the capturing probe is between 8 and 20 nucleotides long.

11. A method according to claim 1 wherein the capturing probe is between 8 and 15 nucleotides long.

12. A method according to claim 1 wherein more than one capturing LNA-probe is used and the capturing probe consist of different LNA-oligomers directed against different target nucleic acids or against different regions of the same nucleic acid.

13. A method according to claim 12, wherein the different capturing probes are spotted in an array format on the solid surface.

14. A method according to claim 13, wherein the array has at least 10 capturing probes.

15. A method according to claim 13, wherein the array has at least 100 capturing probes.

16. A method according to claim 13, wherein the array has at least 1,000 capturing probes.

17. A method according to claim 13, wherein the array has at least 10,000 capturing probes.

18. A method according to claim 1 wherein the nucleic acids originate from cells, a tissue sample or tissue extract.

19. A method according to claim 18, wherein the cells are of archae, prokaryotic, eukaryotic origin.

20. A method according to claim 18, wherein the sample is derived from blood, serum, plasma, reticulocytes, lymphocytes, urine, bone marrow tissue, cerebrospinal fluid or any product prepared from blood or lymph, muscle biopsy, liver biopsy, kidney biopsy, bladder biopsy, bone biopsy, cartilage biopsy, skin biopsy, pancreas biopsy, a biopsy of the intestinal tract, thymus biopsy, mammae biopsy, uterus biopsy, a testicular biopsy, eye biopsy or a brain biopsy, homogenized in lysis buffer.

21. A method according to claim 1 wherein the capturing probe(s) consist(s) of LNA-oligomer(s) directed against one or more target nucleic acid(s) which is/are specific for a specific species of organisms.

22. A method according to claim 1 wherein the capturing probe(s) consist(s) of LNA-oligomer(s) directed against one or more target nucleic acid(s) which is/are specific for a specific species, sub-species or strain of organisms.

23. A method according to claim 1 wherein the capturing probe(s) consist(s) of LNA-oligomer(s) directed against one or more target nucleic acid(s) which is/are specific for a specific species of micro-organisms.

24. A method according to claim 1 wherein the capturing probe(s) consist(s) of LNA-oligomer(s) directed against one or more target nucleic acid(s) which is/are specific for a specific species, sub-species or strain of micro-organisms.

25. A method according to claim 1 wherein the capturing probe(s) consist(s) of LNA-oligomer(s) directed against one or more target nucleic acid(s) which is/are specific for an infectious agent.

26. A method according to claim 1 wherein the capturing probe(s) consist(s) of LNA-oligomer(s) directed against one or more target nucleic acid(s) which is/are specific for a specific species, sub-species or strain of an infectious agent.

27. A method according to claim 1 wherein the capturing probe(s) consist(s) of LNA-oligomer(s) directed against one or more target nucleic acid(s) which is/are specific for genes coding for proteins involved on an inheritable disease.

28. A method according to claim 1 wherein the capturing probe(s) consist(s) of LNA-oligomer(s) directed against one or more target nucleic acid(s) which is/are specific for genes related to a life style disease.

29. A method according to claim 1 wherein the capturing probe(s) consist(s) of LNA-oligomer(s) directed against one or more target nucleic acid(s) which is/are specific for genes related to cancer.

30. A method according to claim 28, wherein the life style diseases are selected from the group consisting of atherosclerosis and diabetes.

31. A method according to claim 1 wherein the solid surface is selected from the group consisting of glass, carbohydrate polymers and metals.

32. A method according to claim 3 wherein the solid surface is the wall in a microtiter plate.

33. A method according to claim 3 wherein the solid has the form of a bead.

34. A method according to claim 3 wherein the solid surface has the form of a flat plate.

35. A method according to claim 1 wherein the isolation is performed in one step.

36. A method according to any of claims 2 and 3, wherein the ligand is biotin.

37. A method according to claim 1 wherein the target nucleic acids hybridized to the capturing probe are detected by a detection probe.

38. A method according to claim 37, wherein the detection probe is labelled with a label elected from the group consisting of fluorophores, radioactive isotopes, enzymes, ligands and haptenic and antigenic compounds.

39. A method according to claim 38, wherein the fluorophore is selected from the group consisting of fluorescein, rhodamin and Texas Red.

40. A method according to claim 38, wherein the radioactive isotope is selected from the group consisting of $^{32}P$, $^{33}P$, $^{35}S$, $^{3}H$, $^{125}I$ and $^{14}C$.

41. A method according to claim 38, wherein the enzyme is selected from the group consisting of horseradish peroxidase, alkaline phosphatase, calf intestine alkaline phosphatase, glucose oxidase and beta-galactosidase.

42. A method according to claim 38, wherein the ligand is selected from the group consisting of biotin, thyroxine and cortisol.

43. A method according to any of claims 37 to 42, wherein the detection probe hybridises to a different region of the immobilised target nucleic acid than the capturing probe.

44. A method according to any of claims 37 to 42, wherein the detecting probe contains at least one LNA-monomer.

45. A method for amplifying a target nucleic acid the nucleotide sequence of which is complementary to the capturing probe, the method comprising the steps of a) providing a sample containing nucleic acids, b) treating the sample with a lysing buffer containing a chaotropic agent to lyse cellular material in the sample, dissolve the components and denature the nucleic acids in the sample, c) contacting the nucleic acids released from the sample with at least one capturing LNA-probe covalently attached to a solid surface, said capturing probe being substantially complementary to the target nucleic acid, d) separating the solid surface from excess material, e) combining the captured nucleic acids with an appropriate amount of nucleoside triphosphates and an agent for polymerisation of the nucleoside triphosphates, f) extending any oligonucleotides which hybridise to the captured nucleic acids to form extension products, wherein the capturing LNA-probes are used as templates, g) detecting the extension product formed.

46. A method for amplifying a target nucleic acid the nucleotide sequence of which is complementary to the capturing probe, the method comprising the steps of a) providing a sample containing nucleic acids, b) treating the sample with a lysing buffer containing a chaotropic agent to lyse cellular material in the sample, dissolve the components and denature the nucleic acids in the sample, c) contacting the nucleic acids released from the sample with at least one capturing LNA-probe covalently attached to a solid surface, said capturing probe being substantially complementary to the target nucleic acid, d) separating the solid surface from excess material, e) combining the captured nucleic acids with an appropriate amount of nucleoside triphosphates and an agent for polymerisation of the nucleoside triphosphates, f) extending any oligonucleotides which hybridise to the captured nucleic acids to form extension products, wherein the capturing LNA-probes are used as templates, g) hybridising, in the presence of an appropriate amount of nucleoside triphosphates and an agent for polymerisation of the nucleoside triphosphates, the single stranded nucleic acids from step c) with at least one downstream primer to synthesise further extension products, h) repeating steps g) through h) a sufficient number of times to result in a detectable amount of extension products, i) detecting the extension products formed.

47. A method for amplifying a target nucleic acid the nucleotide sequence of which is complementary to the capturing probe, the method comprising the steps of a) providing a sample containing nucleic acids, b) treating the sample with a lysing buffer containing a chaotropic agent to lyse cellular material in the sample, dissolve the components and denature the nucleic acids in the sample, c) contacting the nucleic acids released from the sample with at least one capturing LNA-probe covalently attached to a solid surface, said capturing probe being substantially complementary to the target nucleic acid, d) separating the solid surface from excess material, e) combining the captured nucleic acids with an appropriate amount of nucleoside triphosphates, an agent for polymerisation of the nucleoside triphosphates and at least one downstream primer, f) extending any oligonucleotides which hybridise to the captured nucleic acids to form extension products, wherein said nucleic acids are used as templates, g) detecting the extension product formed.

48. A method for amplifying a target nucleic acid the nucleotide sequence of which is complementary to the capturing probe, the method comprising the steps of a) providing a sample containing nucleic acids, b) treating the sample with a lysing buffer containing a chaotropic agent to lyse cellular material in the sample, dissolve the components and denature the nucleic acids in the sample, c) contacting the nucleic acids released from the sample with at least one capturing LNA-probe covalently attached to a solid surface, said capturing probe being substantially complementary to the target nucleic acid, d) separating the solid surface from excess material, e) combining the captured nucleic acids with an appropriate amount of nucleoside triphosphates, an agent for polymerisation of the nucleoside triphosphates and at least one downstream primer, f) extending any oligonucleotides which hybridise to the captured nucleic acids to form extension products, wherein said nucleic acids are used as templates, g) hybridising, in the presence of an appropriate amount of nucleoside triphosphates and an agent for polymerisation of the nucleoside triphosphates, the single stranded nucleic acids from step c) with at least one downstream primer to synthesise further extension products, h) repeating steps g) through h) a sufficient number of times to result in a detectable amount of extension products, i) detecting the extension products formed.

49. A kit for isolating a target nucleic acid comprising a) a lysing buffer containing a chaotropic agent to lyse cellular material in the sample, b) at least one capturing LNA-probe, said capturing probe being substantially complementary to the target nucleic acid.

50. A method of claim 1 wherein the sample is treated with the chaotropic lysing buffer and the nucleic acids are contacted with the LNA-probe in a single reaction vessel without a wash step between the treating and contacting.

51. A method of claim 50 wherein the lysing buffer comprises a guanidine compound.

52. A method of claim 50 wherein nucleic acid hybridised to the LNA-probe are detected.

53. A method for isolating a target nucleic acid comprising:

a) providing a cellular sample containing nucleic acids;

b) treating the sample with a lysing buffer containing a guanidine compound; and c) contacting the nucleic acids released from the sample with at least one capturing LNA-probe, the LNA-probe being substantially complementary to the target nucleic acid.

54. A method of claim 53 further comprising detecting nucleic acid hybridised to the LNA-probe.

55. A method of claim 53 wherein the sample is treated with the lysing buffer and the nucleic acids are contacted with the LNA-probe in a single reaction vessel without a wash step between the treating and contacting.

56. A method of claim 54 wherein the sample is treated with the lysing buffer, the nucleic acids are contacted with the LNA-probe, and the nucleic acid hybridized to the LNA-probe are detected in a single reaction vessel without a wash step between the treating, contacting and detecting.

57. A method of claim 53 wherein the guanidine compound is guanidine thiocyanate or guanidine hydrochloride.

58. A method for isolating a target nucleic acid comprising:

a) providing a cellular sample containing nucleic acids;

b) treating the sample with a lysing composition; and c) contacting the nucleic acids released from the sample with at least one capturing LNA-probe, the LNA-probe containing a total of from 4 to 20 nucleotides and being substantially complementary to the target nucleic acid.

59. A method of claim 58 further comprising detecting nucleic acid hybridised to the LNA-probe.

60. A method of claim 58 wherein the sample is treated with the lysing buffer and the nucleic acids are contacted with the LNA-probe in a single reaction vessel without a wash step between the treating and contacting.

61. A method of claim 58 wherein the sample is treated with the lysing buffer, the nucleic acids are contacted with the LNA-probe, and the nucleic acid hybridized to the LNA-probe are detected in a single reaction vessel without a wash step between the treating, contacting and detecting.

62. A method of claim 58 wherein the lysing composition comprises a guanidine compound.

63. A method of claim 62 wherein the guanidine compound is guanidine thiocyanate or guanidine hydrochloride.

64. A method of claim 58 wherein the LNA probe contains a total of from 8 to 20 nucleotides.

65. A method of claim 58 wherein the LNA probe contains a total of from 8 to 15 nucleotides.

* * * * *

```
                          SEQUENCE LISTING

<160> NUMBER OF SEQ ID NOS: 18

<210> SEQ ID NO 1
<211> LENGTH: 50
<212> TYPE: DNA
<213> ORGANISM: Homo Sapiens

<400> SEQUENCE: 1
cttacttgaa ttccaagagc acacggtctt cagtgaagct gcagggcact            50

<210> SEQ ID NO 2
<211> LENGTH: 50
<212> TYPE: DNA
<213> ORGANISM: Homo Sapiens

<400> SEQUENCE: 2
cttacttgaa ttccaagagc acacagtctt cagtgaagct gcagggcact            50

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
gtttttcgta ctgtgctccc agag                                       24

<210> SEQ ID NO 4
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)...(23)
<223> OTHER INFORMATION: LNA
<220> FEATURE:
<221> NAME/KEY: misc_feature
<222> LOCATION: (18)...(19)
<223> OTHER INFORMATION: 5-methyl-cytosine LNA

<400> SEQUENCE: 4
tacatgttat gctttgaccg tgtg                                       24

<210> SEQ ID NO 5
<211> LENGTH: 27
<212> TYPE: DNA
<213> ORGANISM: SyArtificial Sequence
<220> FEATURE:
<223> OTHER INFORMATION: Synthethic primer
<220> FEATURE:
<221> NAME/KEY: misc_feature
<222> LOCATION: (16)...(26)
<223> OTHER INFORMATION: LNA
<220> FEATURE:
<221> NAME/KEY: misc_feature
<222> LOCATION: (20)...(21)
<223> OTHER INFORMATION: 5-methyl-cytosine LNA
```

```
<400> SEQUENCE: 5
tacatgttat gctttaagac cgtgtgc                                    27

<210> SEQ ID NO 6
<211> LENGTH: 9
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)...(9)
<223> OTHER INFORMATION: LNA
<220> FEATURE:
<221> NAME/KEY: misc_feature
<222> LOCATION: (1)...(1)
<223> OTHER INFORMATION: 5-hexaethylenglycol LNA
<220> FEATURE:
<221> NAME/KEY: misc_feature
<222> LOCATION: (4)...(4)
<223> OTHER INFORMATION: 5-methyl-cytosine LNA

<400> SEQUENCE: 6 agaccgtgt                                                         9

<210> SEQ ID NO 7
<211> LENGTH: 50
<212> TYPE: DNA
<213> ORGANISM: Homo Sapiens

<400> SEQUENCE: 7
ttgaattcca agagcacacg gtcttcagtg aagctgcagg gcacttccaa            50

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ttggaagtgc cctgcagctt                                            20

<210> SEQ ID NO 9
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)...(23)
<223> OTHER INFORMATION: LNA
<220> FEATURE:
<221> NAME/KEY: misc_feature
<222> LOCATION: (18)...(18)
<223> OTHER INFORMATION: 5-methyl-cytosine LNA

<400> SEQUENCE: 9
tacatgttat gctttgactg tgtg                                       24

<210> SEQ ID NO 10
<211> LENGTH: 50
<212> TYPE: DNA
<213> ORGANISM: Homo Sapiens

<400> SEQUENCE: 10
ttgaattcca agagcacaca gtcttcagtg aagctgcagg gcacttccaa            50
```

```
<210> SEQ ID NO 11
<211> LENGTH: 9
<212> TYPE: DNA
<213> ORGANISM: Artificial Sequence
<220> FEATURE:
<223> OTHER INFORMATION: Synthethic primer
<220> FEATURE:
<221> NAME/KEY: misc_feature
<222> LOCATION: (1)...(8)
<223> OTHER INFORMATION: LNA
<220> FEATURE:
<221> NAME/KEY: misc_feature
<222> LOCATION: (1)...(1)
<223> OTHER INFORMATION: 5-methyl-cytosine LNA
<220> FEATURE:
<221> NAME/KEY: misc_feature
<222> LOCATION: (3)...(3)
<223> OTHER INFORMATION: 5-methyl-cytosine LNA
<220> FEATURE:
<221> NAME/KEY: misc_feature
<222> LOCATION: (5)...(5)
<223> OTHER INFORMATION: 5-methyl-cytosine LNA
<220> FEATURE:
<221> NAME/KEY: misc_feature
<222> LOCATION: (7)...(7)
<223> OTHER INFORMATION: 5-methyl-cytosine LNA

<400> SEQUENCE: 11 cgcacacgt                                                                 9

<210> SEQ ID NO 12
<211> LENGTH: 9
<212> TYPE: DNA
<213> ORGANISM: Artificial Sequence
<220> FEATURE:
<223> OTHER INFORMATION: Synthetic primer

<400> SEQUENCE: 12 acgtgtgcg                                                                 9

<210> SEQ ID NO 13
<211> LENGTH: 9
<212> TYPE: DNA
<213> ORGANISM: Artificial Sequence
<220> FEATURE:
<223> OTHER INFORMATION: Synthetic primer

<400> SEQUENCE: 13 acgtgcgcg                                                                 9

<210> SEQ ID NO 14
<211> LENGTH: 9
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)...(8)
<223> OTHER INFORMATION: LNA
<220> FEATURE:
<221> NAME/KEY: misc_feature
<222> LOCATION: (3)...(3)
<223> OTHER INFORMATION: 5-methyl-cytosine LNA
<220> FEATURE:
<221> NAME/KEY: misc_feature
<222> LOCATION: (5)...(5)
<223> OTHER INFORMATION: 5-methyl-cytosine LNA
<220> FEATURE:
<221> NAME/KEY: misc_feature
<222> LOCATION: (8)...(8)
```

```
<223> OTHER INFORMATION: 5-methyl-cytosine LNA

<400> SEQUENCE: 14 ggcacttct                                                                    9

<210> SEQ ID NO 15
<211> LENGTH: 9
<212> TYPE: DNA
<213> ORGANISM: Artificial Sequence
<220> FEATURE:
<223> OTHER INFORMATION: synthetic primer

<400> SEQUENCE: 15 agaagtgcc                                                                    9

<210> SEQ ID NO 16
<211> LENGTH: 9
<212> TYPE: DNA
<213> ORGANISM: Artificial Sequence
<220> FEATURE:
<223> OTHER INFORMATION: Synthetic primer

<400> SEQUENCE: 16 agaagcgcc                                                                    9

<210> SEQ ID NO 17
<211> LENGTH: 35
<212> TYPE: DNA
<213> ORGANISM: Artificial Sequence
<220> FEATURE:
<223> OTHER INFORMATION: Synthetic primer

<400> SEQUENCE: 17
ctagtgaggc caacacttac ttgaattcca agagc                                      35

<210> SEQ ID NO 18
<211> LENGTH: 27
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)...(26)
<223> OTHER INFORMATION: LNA
<220> FEATURE:
<221> NAME/KEY: misc_feature
<222> LOCATION: (20)...(20)
<223> OTHER INFORMATION: 5-methyl-cytosine LNA

<400> SEQUENCE: 18
tacatgttat gctttaagac tgtgtgc                                               27
```